US007326237B2

(12) United States Patent
DePalma et al.

(10) Patent No.: US 7,326,237 B2
(45) Date of Patent: Feb. 5, 2008

(54) SUPRA-RENAL ANCHORING PROSTHESIS

(75) Inventors: Donald F. DePalma, Weston, FL (US);
Clifford J. Dwyer, Weston, FL (US);
Robert P. Letendre, Hialeah, FL (US)

(73) Assignee: Cordis Corporation, Miami Lakes, FL (US)

( * ) Notice: Subject to any disclaimer, the term of this patent is extended or adjusted under 35 U.S.C. 154(b) by 678 days.

(21) Appl. No.: 10/041,116

(22) Filed: Jan. 8, 2002

(65) Prior Publication Data

US 2003/0130724 A1 Jul. 10, 2003

(51) Int. Cl.
*A61F 2/06* (2006.01)
(52) U.S. Cl. ..................................... 623/1.13
(58) Field of Classification Search ............... 623/1.13, 623/1.35, 1.12, 1.15, 1.11
See application file for complete search history.

(56) References Cited

U.S. PATENT DOCUMENTS

| 3,585,707 A | 6/1971 | Stevens |
| 3,657,744 A | 4/1972 | Ersek |
| 4,169,464 A | 10/1979 | Obrez |
| 4,187,390 A | 2/1980 | Gore |
| 4,317,451 A | 3/1982 | Cerwin et al. |
| 4,441,216 A | 4/1984 | Ionescu et al. |
| RE31,618 E | 7/1984 | Mano |
| 4,503,569 A | 3/1985 | Dotter |
| 4,553,545 A | 11/1985 | Maass |
| 4,562,596 A | 1/1986 | Kornberg |
| 4,580,568 A | 4/1986 | Gianturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes |
| 4,731,073 A | 3/1988 | Robinson |
| 4,732,152 A | 3/1988 | Wallsten |
| 4,733,665 A | 3/1988 | Palmaz |
| 4,739,762 A | 4/1988 | Palmaz |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 4,856,516 A | 8/1989 | Hillstead |
| 4,875,480 A | 10/1989 | Imbert |
| 4,886,062 A | 12/1989 | Wiktor |

(Continued)

FOREIGN PATENT DOCUMENTS

DE 3205942 A1 9/1983

(Continued)

*Primary Examiner*—(Jackie) Tan-Uyen Ho
*Assistant Examiner*—Melanie Tyson

(57) ABSTRACT

A system, apparatus, and method for treating, repairing, an aneurysm, preferably an aortic aneurysm, and most preferably, an abdominal aortic aneurysm as described herein. The systems, devices, and methods described herein include a first prosthesis or stent gasket, and at least one second prosthesis for bypassing the aneurysm. The first prosthesis is configured and adapted to accommodate a section of artery upstream of the aneurysm, wherein the section is unsuitable for anchoring a typical first prosthesis.

3 Claims, 23 Drawing Sheets

U.S. PATENT DOCUMENTS

| | | |
|---|---|---|
| 4,907,336 A | 3/1990 | Gianturco |
| 4,913,141 A | 4/1990 | Hillstead |
| 4,925,445 A | 5/1990 | Sakamoto |
| 4,950,227 A | 8/1990 | Savin |
| 4,955,899 A | 9/1990 | Della Corna |
| 4,969,458 A | 11/1990 | Wiktor |
| 4,990,131 A | 2/1991 | Dardik |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton |
| 5,035,694 A | 7/1991 | Kasprzyk et al. |
| 5,035,706 A | 7/1991 | Gianturco |
| 5,041,126 A | 8/1991 | Gianturco |
| 5,045,072 A | 9/1991 | Castillo |
| 5,064,435 A | 11/1991 | Porter |
| 5,078,726 A | 1/1992 | Kreamer |
| 5,084,065 A | 1/1992 | Weldon |
| 5,100,422 A | 3/1992 | Berguer |
| 5,102,417 A | 4/1992 | Palmaz |
| 5,104,399 A | 4/1992 | Lazarus |
| 5,104,400 A | 4/1992 | Berguer |
| 5,104,404 A | 4/1992 | Wolff |
| 5,114,423 A | 5/1992 | Kasprzyk et al. |
| 5,116,365 A | 5/1992 | Hillstead |
| 5,122,154 A | 6/1992 | Rhodes |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi |
| 5,156,620 A | 10/1992 | Pigott |
| 5,159,920 A | 11/1992 | Cordon |
| 5,163,951 A | 11/1992 | Pinchuk |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Hull |
| 5,192,307 A | 3/1993 | Wall |
| 5,195,984 A | 3/1993 | Schatz |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi |
| 5,222,971 A | 6/1993 | Willard et al. |
| 5,236,447 A | 8/1993 | Kubo |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno |
| 5,290,305 A | 3/1994 | Inoue |
| 5,292,331 A | 3/1994 | Boneau |
| 5,304,197 A | 4/1994 | Pinchuk |
| 5,304,200 A | 4/1994 | Spaulding |
| 5,306,294 A | 4/1994 | Winston |
| 5,314,444 A | 5/1994 | Gianturco |
| 5,314,472 A | 5/1994 | Fontaine |
| 5,316,023 A | 5/1994 | Palmaz |
| 5,318,535 A | 6/1994 | Miraki |
| 5,321,109 A | 6/1994 | Bosse |
| 5,330,490 A | 7/1994 | Wilk |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summersq |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone |
| 5,366,473 A | 11/1994 | Winston |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,328 A | 1/1995 | Morgan |
| 5,382,261 A | 1/1995 | Palmaz |
| 5,383,927 A | 1/1995 | DeGoicoechea |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Solar |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,453,090 A | 9/1995 | Martinez et al. |
| 5,453,235 A | 9/1995 | Calcote |
| 5,456,713 A | 10/1995 | Chuter |
| 5,466,509 A | 11/1995 | Kowligi |
| 5,468,138 A | 11/1995 | Bosse |
| 5,476,506 A | 12/1995 | Lunn |
| 5,480,423 A | 1/1996 | Ravenscroft |
| 5,484,444 A | 1/1996 | Braunchweiler |
| 5,489,295 A | 2/1996 | Piplani et al. |
| 5,496,365 A | 3/1996 | Sgro |
| 5,507,767 A | 4/1996 | Maeda et al. |
| 5,507,769 A | 4/1996 | Marin |
| 5,507,771 A | 4/1996 | Gianturco |
| 5,507,995 A | 4/1996 | Schweich, Jr. et al. |
| 5,512,229 A | 4/1996 | Bosse |
| 5,522,880 A | 6/1996 | Barone |
| 5,522,882 A | 6/1996 | Gaterud |
| 5,527,354 A | 6/1996 | Fontaine et al. |
| 5,549,662 A | 8/1996 | Fordenbacher |
| 5,549,663 A | 8/1996 | Cottone, Jr. |
| 5,562,698 A | 10/1996 | Parker |
| 5,562,724 A | 10/1996 | Vorwerk |
| 5,562,726 A | 10/1996 | Chuter |
| 5,569,295 A | 10/1996 | Lam |
| 5,571,170 A | 11/1996 | Palmaz |
| 5,571,171 A | 11/1996 | Barone |
| 5,571,173 A | 11/1996 | Parodi |
| 5,578,071 A | 11/1996 | Parodi |
| 5,578,072 A | 11/1996 | Barone |

| | | | | | |
|---|---|---|---|---|---|
| 5,591,196 A | 1/1997 | Marin et al. | 5,755,735 A | 5/1998 | Richter et al. |
| 5,591,197 A | 1/1997 | Orth et al. | 5,755,770 A | 5/1998 | Ravenscroft |
| 5,591,228 A | 1/1997 | Edoga | 5,755,771 A | 5/1998 | Penn et al. |
| 5,591,229 A | 1/1997 | Parodi | 5,755,772 A | 5/1998 | Evans et al. |
| 5,593,412 A | 1/1997 | Martinez et al. | 5,755,773 A | 5/1998 | Evans et al. |
| 5,607,444 A | 3/1997 | Lam | 5,755,777 A | 5/1998 | Chuter |
| 5,607,464 A | 3/1997 | Trescony et al. | 5,758,562 A | 6/1998 | Thompson |
| 5,609,624 A | 3/1997 | Kalis | 5,760,006 A | 6/1998 | Shank |
| 5,609,625 A | 3/1997 | Piplani et al. | 5,766,201 A | 6/1998 | Ravenscroft et al. |
| 5,609,627 A | 3/1997 | Goicoechea et al. | 5,769,882 A | 6/1998 | Fogarty et al. |
| 5,617,878 A | 4/1997 | Taheri | 5,769,885 A | 6/1998 | Quiachon et al. |
| 5,618,300 A | 4/1997 | Marin et al. | 5,776,180 A | 7/1998 | Goicoechea et al. |
| 5,628,783 A | 5/1997 | Quiachon et al. | 5,782,765 A | 7/1998 | Jonkman |
| 5,628,786 A | 5/1997 | Banas | 5,782,906 A | 7/1998 | Marshall et al. |
| 5,628,788 A | 5/1997 | Pinchuk | 5,782,909 A | 7/1998 | Quiachon et al. |
| 5,632,763 A | 5/1997 | Glastra | 5,788,626 A | 8/1998 | Thompson |
| 5,632,778 A | 5/1997 | Goldstein | 5,797,953 A | 8/1998 | Tekulve |
| 5,639,278 A | 6/1997 | Dereume et al. | 5,800,456 A | 9/1998 | Maeda et al. |
| 5,641,443 A | 6/1997 | Calcote et al. | 5,800,508 A | 9/1998 | Goicoechea et al. |
| 5,643,312 A | 7/1997 | Fischell et al. | 5,800,516 A | 9/1998 | Fine et al. |
| 5,645,559 A | 7/1997 | Hachtman | 5,800,518 A | 9/1998 | Piplani et al. |
| 5,649,952 A | 7/1997 | Lam | 5,800,520 A | 9/1998 | Fogarty et al. |
| 5,653,743 A | 8/1997 | Martin | 5,810,870 A | 9/1998 | Myers |
| 5,653,745 A | 8/1997 | Trescony et al. | 5,824,036 A | 10/1998 | Lauterjung |
| 5,653,747 A | 8/1997 | Dereume | 5,824,037 A | 10/1998 | Fogarty et al. |
| 5,662,700 A | 9/1997 | Lazarus | 5,824,039 A | 10/1998 | Piplani et al. |
| 5,662,703 A | 9/1997 | Yurek et al. | 5,824,040 A | 10/1998 | Cox et al. |
| 5,665,117 A * | 9/1997 | Rhodes ................. 623/1.1 | 5,824,041 A | 10/1998 | Lenker et al. |
| 5,667,523 A | 9/1997 | Bynon | 5,824,042 A | 10/1998 | Lombardi et al. |
| 5,669,924 A | 9/1997 | Shaknovich | 5,824,043 A | 10/1998 | Cottone, Jr. |
| 5,669,936 A | 9/1997 | Lazarus | 5,824,046 A | 10/1998 | Smith |
| 5,674,241 A | 10/1997 | Bley | 5,824,054 A | 10/1998 | Khosravi |
| 5,674,276 A | 10/1997 | Andersen et al. | 5,824,055 A | 10/1998 | Spiridigliozzi et al. |
| 5,676,696 A | 10/1997 | Marcade | 5,827,044 A | 10/1998 | Yazici et al. |
| 5,676,697 A | 10/1997 | McDonald | 5,827,310 A | 10/1998 | Marin et al. |
| 5,681,345 A | 10/1997 | Euteneuer | 5,827,320 A | 10/1998 | Richter et al. |
| 5,681,346 A | 10/1997 | Orth et al. | 5,827,327 A | 10/1998 | McHaney |
| 5,683,448 A | 11/1997 | Cragg | 5,830,229 A | 11/1998 | Konya et al. |
| 5,683,449 A | 11/1997 | Marcade | 5,833,651 A | 11/1998 | Donovan et al. |
| 5,683,450 A | 11/1997 | Goicoechea et al. | 5,840,011 A | 11/1998 | Landgrebe et al. |
| 5,683,451 A | 11/1997 | Lenker et al. | 5,843,031 A | 12/1998 | Hermann et al. |
| 5,685,847 A | 11/1997 | Barry | 5,843,120 A | 12/1998 | Israel |
| 5,693,083 A | 12/1997 | Baker et al. | 5,843,158 A | 12/1998 | Lenker et al. |
| 5,693,084 A | 12/1997 | Chuter | 5,843,160 A | 12/1998 | Rhodes |
| 5,693,085 A | 12/1997 | Buirge et al. | 5,855,598 A | 1/1999 | Pinchuk |
| 5,693,086 A | 12/1997 | Goicoechea et al. | 5,857,998 A | 1/1999 | Barry |
| 5,695,517 A | 12/1997 | Marin et al. | 5,858,556 A | 1/1999 | Eckert |
| 5,697,948 A | 12/1997 | Marin et al. | 5,860,998 A | 1/1999 | Robinson et al. |
| 5,697,971 A | 12/1997 | Fischell et al. | 5,861,027 A | 1/1999 | Trapp |
| 5,700,285 A | 12/1997 | Myers | 5,868,777 A | 2/1999 | Lam |
| 5,702,418 A | 12/1997 | Ravenscroft | 5,871,537 A | 2/1999 | Holman et al. |
| 5,713,917 A | 2/1998 | Leonhardt et al. | 5,871,538 A | 2/1999 | Dereume |
| 5,716,365 A | 2/1998 | Goicoechea et al. | 5,876,397 A | 3/1999 | Edelman et al. |
| 5,718,159 A | 2/1998 | Thompson | 5,893,868 A | 4/1999 | Hanson et al. |
| 5,718,724 A | 2/1998 | Goicoechea et al. | 5,893,887 A | 4/1999 | Jayaraman |
| 5,720,735 A | 2/1998 | Dorros | 5,899,890 A | 5/1999 | Chiang et al. |
| 5,720,776 A | 2/1998 | Chuter et al. | 5,902,308 A | 5/1999 | Murphy |
| 5,723,003 A | 3/1998 | Winston | 5,904,713 A | 5/1999 | Leschinsky |
| 5,723,004 A | 3/1998 | Dereume et al. | 5,906,619 A | 5/1999 | Olson et al. |
| 5,725,534 A | 3/1998 | Rasmussen | 5,906,640 A | 5/1999 | Penn et al. |
| 5,725,568 A | 3/1998 | Hastings | 5,906,641 A | 5/1999 | Thompson et al. |
| 5,725,570 A | 3/1998 | Heath | 5,908,448 A | 6/1999 | Roberts et al. |
| 5,728,065 A | 3/1998 | Follmer et al. | 5,916,263 A | 6/1999 | Goicoechea et al. |
| 5,728,068 A | 3/1998 | Leone et al. | 5,916,264 A | 6/1999 | Von Oepen |
| 5,728,131 A | 3/1998 | Frantzen et al. | 5,919,224 A | 7/1999 | Thompson et al. |
| 5,733,328 A | 3/1998 | Fordenbacher | 5,928,260 A | 7/1999 | Chin et al. |
| 5,735,892 A | 4/1998 | Myers | 5,935,667 A | 8/1999 | Calcote |
| 5,746,709 A | 5/1998 | Rom et al. | 5,938,696 A | 8/1999 | Goicoechea et al. |
| 5,749,880 A | 5/1998 | Banas | 5,944,726 A | 8/1999 | Blaeser et al. |
| 5,749,920 A | 5/1998 | Quiachon et al. | 5,944,750 A | 8/1999 | Tanner et al. |
| 5,749,921 A | 5/1998 | Lenker et al. | 5,951,599 A | 9/1999 | McCrory |
| 5,752,966 A | 5/1998 | Chang | 5,954,693 A | 9/1999 | Barry |
| 5,755,734 A | 5/1998 | Richter et al. | 5,957,973 A | 9/1999 | Quiachon et al. |

| | | |
|---|---|---|
| 5,957,974 A | 9/1999 | Thompson et al. |
| 5,961,548 A | 10/1999 | Shmulewitz |
| 5,968,069 A | 10/1999 | Dusbabek et al. |
| 5,968,088 A | 10/1999 | Hansen et al. |
| 5,980,565 A | 11/1999 | Jayaraman |
| 5,993,481 A | 11/1999 | Marcade et al. |
| 6,007,543 A | 12/1999 | Ellis et al. |
| 6,015,431 A | 1/2000 | Thornton et al. |
| 6,015,432 A | 1/2000 | Rakos et al. |
| 6,016,810 A | 1/2000 | Ravenscroft |
| 6,017,363 A | 1/2000 | Hojeibane |
| 6,017,364 A | 1/2000 | Lazarus |
| 6,019,778 A | 2/2000 | Wilson et al. |
| 6,019,786 A | 2/2000 | Thompson |
| 6,024,763 A | 2/2000 | Lenker et al. |
| 6,027,526 A | 2/2000 | Limon et al. |
| 6,027,529 A | 2/2000 | Roychowdhury et al. |
| 6,030,413 A | 2/2000 | Lazarus |
| 6,030,415 A | 2/2000 | Chuter |
| 6,033,435 A | 3/2000 | Penn et al. |
| 6,036,697 A | 3/2000 | DiCaprio |
| 6,036,723 A | 3/2000 | Anidjar et al. |
| 6,036,725 A | 3/2000 | Avellanet |
| 6,039,749 A | 3/2000 | Marin et al. |
| 6,039,758 A | 3/2000 | Quiachon et al. |
| 6,048,356 A | 4/2000 | Ravenscroft et al. |
| 6,051,020 A | 4/2000 | Goicoechea et al. |
| 6,056,775 A | 5/2000 | Borghi et al. |
| 6,059,821 A | 5/2000 | Anidjar et al. |
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,077,273 A | 6/2000 | Euteneuer et al. |
| 6,078,832 A | 6/2000 | Lenker et al. |
| 6,086,577 A | 7/2000 | Ken et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,093,199 A | 7/2000 | Brown et al. |
| 6,097,978 A | 8/2000 | Demarais et al. |
| 6,099,558 A | 8/2000 | White et al. |
| 6,099,560 A | 8/2000 | Penn et al. |
| 6,102,938 A | 8/2000 | Evans et al. |
| 6,102,942 A | 8/2000 | Ahari |
| 6,110,191 A | 8/2000 | Dehdashtian et al. |
| 6,110,198 A | 8/2000 | Fogarty et al. |
| 6,117,117 A | 9/2000 | Mauch |
| 6,117,156 A | 9/2000 | Richter et al. |
| 6,117,157 A | 9/2000 | Tekulve |
| 6,117,167 A | 9/2000 | Goicoechea et al. |
| 6,123,722 A | 9/2000 | Fogarty et al. |
| 6,126,685 A | 10/2000 | Lenker et al. |
| 6,129,754 A | 10/2000 | Kaneska et al. |
| 6,132,450 A | 10/2000 | Hanson et al. |
| 6,132,459 A | 10/2000 | Piplani et al. |
| 6,152,956 A * | 11/2000 | Pierce ........................ 623/1.13 |
| 6,280,466 B1 * | 8/2001 | Kugler et al. ............... 623/1.12 |
| 6,302,906 B1 | 10/2001 | Goicoechea et al. |
| 6,306,164 B1 * | 10/2001 | Kujawski ................... 623/1.35 |
| 6,325,819 B1 | 12/2001 | Pavenik et al. |
| 2001/0053930 A1 | 12/2001 | Kugler et al. |

FOREIGN PATENT DOCUMENTS

| | | |
|---|---|---|
| EP | 0 540 290 A3 | 5/1993 |
| EP | 0579523 A1 | 1/1994 |
| EP | 0657147 A2 | 10/1994 |
| EP | 0686379 B1 | 12/1995 |
| EP | 734698 A2 | 10/1996 |
| EP | 783873 A2 | 7/1997 |
| EP | 800801 A1 | 10/1997 |
| EP | 830853 A1 | 3/1998 |
| EP | 832616 A1 | 4/1998 |
| EP | 0855170 A2 | 7/1998 |
| EP | 880948 A1 | 12/1998 |
| EP | 0928606 A1 | 7/1999 |
| EP | 937442 A2 | 8/1999 |
| EP | 0947179 A2 | 10/1999 |
| EP | 1000590 A1 | 5/2000 |
| EP | 1212988 A | 6/2002 |
| FR | 0 566 807 A1 | 2/1924 |
| FR | 2733682 A1 | 11/1996 |
| FR | 2740346 A1 | 4/1997 |
| FR | 2743293 A1 | 7/1997 |
| GB | 0 662 307 A2 | 9/1948 |
| GB | 1 205 743 | 9/1970 |
| JP | 5524095 A | 2/1980 |
| JP | 60220030 A | 11/1985 |
| JP | 62231657 A | 3/1988 |
| JP | 464367 A | 2/1992 |
| JP | 4263852 A | 4/1992 |
| JP | 5 76603 A | 3/1993 |
| JP | 5 269199 A | 10/1993 |
| JP | 7529 A | 10/1994 |
| JP | 6282730 A | 10/1994 |
| JP | 7 24072 A | 1/1995 |
| JP | 7100210 A | 4/1995 |
| JP | 6 86827 A | 6/1998 |
| SU | 1680055 | 5/1988 |
| WO | 8704935 A1 | 8/1987 |
| WO | 9516406 A1 | 6/1995 |
| WO | 9521592 A1 | 8/1995 |
| WO | 9626689 A1 | 9/1996 |
| WO | 96/34580 A1 | 11/1996 |
| WO | 9724081 A1 | 7/1997 |
| WO | 9725000 A1 | 7/1997 |
| WO | 9733532 A2 | 9/1997 |
| WO | 9807389 A1 | 2/1998 |
| WO | 98/19628 A1 | 5/1998 |
| WO | 9823322 A1 | 6/1998 |
| WO | 9836709 A1 | 8/1998 |
| WO | 9853761 A1 | 12/1998 |
| WO | 9908744 A1 | 2/1999 |
| WO | 9911199 A1 | 3/1999 |
| WO | WO 01/49211 A | 7/2001 |

* cited by examiner

SUPRA-RENAL ANCHORING PROSTHESIS

BACKGROUND OF THE INVENTION

1. Field of the Invention

The present invention relates to devices and methods for repairing aneurysms, and more particularly, to percutaneously and/or intraluminally delivered devices and methods for repairing aneurysms, such as abdominal aortic aneurysms and thoracic aortic aneurysms.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital, and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e. catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. Their delivery procedure typically involves advanced angiographic techniques performed through vascular accesses gained via surgical cutdown of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

As will be recognized by those skilled in the art, placing a prosthesis upstream of an aneurysm requires a sufficient length of suitable artery within which to anchor an upstream portion of the prosthesis. For some patients, a suitable length of artery upstream of the aneurysm is not available. For example, a Schumacher Type III abdominal aortic aneurysm is typically characterized by a short infra-renal neck (i.e., the section of the artery downstream of the renal arteries and upstream of an aneurysm is typically less than about 15 mm) and/or a high angulated neck (greater than about 45). In both of these circumstances, it is typically not possible to implant a prosthesis upstream of the aneurysm without blocking one or both of the renal arteries. Also, the shape, angle, or length of the existing artery may prevent achieving a fluid tight connection between the prosthesis and the arterial wall.

Therefore, a need exists for a prosthesis specifically designed to accommodate a short section of artery, to accommodate a section of artery that includes an arterial junction, and/or to accommodate a highly angulated section of artery.

SUMMARY OF THE INVENTION

The suprarenal anchoring prosthesis of the present invention provides a means for overcoming the problems associated with anchoring and/or sealing a prosthesis in an artery that is highly angulated, too short for proper positioning and/or otherwise diseased as briefly described above.

The present invention is directed to a system including at least one prosthesis for repair or replacement of a mammalian body part or condition. The typical system includes a first prosthesis for anchoring and sealing the system within a predetermined portion of an artery; at least one second prosthesis engaged to the first prosthesis, the second prosthesis providing a fluid flow path through the system or a portion of the system; and a third or extension prosthesis for extending a fluid flow path through the system or a portion of the system. In some exemplary embodiments of the invention, the second prosthesis is sealingly and/or matingly engaged with the first prosthesis. In some exemplary embodiments of the invention, the extension prosthesis extends the fluid flow path formed by the second prosthesis. In some exemplary embodiments of the invention, the extension prosthesis is sealingly and/or matingly engaged with the second prosthesis.

In accordance with the present invention, the predetermined position, as used herein, refers to a section of an artery upstream of an aneurysm, the section being unsuitable for anchoring a prosthesis. In accordance with the present invention, a section is unsuitable if it is too short, too bent or angulated, includes another artery (typically, a cross-flow artery), or any other condition in which it would be desirable or beneficial to anchor the prosthesis upstream of the unsuitable section of artery. A section is also unsuitable if it would be deleterious to place a fluid tight prosthesis within a section of artery in which continued blood flow is desirable.

A typical first prosthesis includes a support or stent structure, and a foam or gasket material supported by the stent, the stent and gasket material being configured to seal the system within an artery. A typical first prosthesis also includes one or more structures or elements for engaging the second prosthesis. In exemplary embodiments of the invention, these elements or structures sealingly and/or matingly engage the second prosthesis. The stent is typically a synthetic or natural matrix for supporting the gasket material. In some exemplary embodiments of the stent, the stent is a hollow, substantially cylindrical, and preferably radially expandable matrix having a lumen and two open ends. The typical gasket material is a synthetic or natural fabric, tissue, foam, or the like. In preferred embodiments of the invention, the gasket material covers at least a portion of the lumen, even more preferably, the proximal end of the lumen.

The typical second prosthesis of the present invention includes a support or stent structure, and graft material supported by the stent, the stent and graft material defining a fluid flow path therethrough. The typical graft material is a synthetic or natural fabric, tissue, or the like. The stent is typically a synthetic or natural matrix for supporting the graft and/or positioning the prosthesis in a pre-determined position. In some exemplary embodiments of the stent, the stent is a hollow, substantially cylindrical, and preferably radially expandable matrix having a lumen and two open ends. The stent typically comprises a plurality of interconnected struts. In some exemplary embodiments of the invention, a graft material may be positioned on an inside and/or outside surface of the matrix; in preferred embodiments of the invention, the graft material may include a plurality of substantially longitudinally directed pleats disposed thereon. In a particularly preferred embodiment, the graft further includes a plurality of radially oriented pleat interruptions. In some exemplary embodiments of the invention the graft material may be attached to the stent, preferably by one or more staples or the like.

A prosthesis according to the present invention is specifically adapted and configured for an unsuitable section of artery or the like upstream of an aneurysm. These specific adaptations and configurations include, but are not limited to an elongated proximal stent; an elongated proximal stent having a flow through intermediate section, e.g., a section without graft material; a proximal stent portion having a pivot, joint, axis, juncture, hinge, hub or the like to provide an angled prosthesis; and combinations thereof. A prosthesis according to the present invention for supra-renal anchoring comprises a flexible design both proximally and distally.

A system according to the present invention is intended for repairing or bypassing an aneurysm, preferably an aortic aneurysm. The system may also be used to direct fluid flow from one portion of a fluid pathway to another. The system may also be used for repairing or bypassing aneurysms having an upstream portion unsuitable for anchoring or using a typical prosthesis.

A system of the present invention may comprise various components, elements, and/or prostheses, the combination of which preferably provide four functions:

1) an anchor positioned upstream of a cross artery, providing an anchoring function for the system; the typical anchor comprises an uncovered stent portion configured to have greater radial force against the wall of the artery;

2) a trans- or para-region that spans the cross artery, providing a flexible and open connection between the upstream portion of the system and the downstream portion; the typical trans-region comprises a flexible uncovered stent portion or bridge section;

3) a fluid tight seal, providing a sealing function that prevents fluid leakage outside the system; the typical sealing element or prosthesis is positioned downstream of the cross artery, and includes a sealing diaphragm configured to seat another element or prosthesis that defines a fluid flow path; the radial fluid tight seal is accomplished by the oversize of the second prosthesis in the first prosthesis pinning the first prosthesis against healthy tissue in the vessel, essentially the bottom portion of the first prosthesis seals, retains and orients the longitudinally flexible second prosthesis; and 4) a delivery system guide, providing a guiding function for the various elements of the delivery system; the typical guide is a flared portion of the downstream end of the system, said flared portion providing proper orientation or channeling of the catheter elements used to deliver the various components of the system.

The accompanying figures show illustrative exemplary embodiments of the invention from which these and other of the objectives, novel features and advantages will be readily apparent.

BRIEF DESCRIPTION OF THE DRAWINGS

The foregoing and other aspects of the present invention will best be appreciated with reference to the detailed description of the invention in conjunction with the accompanying drawings. Throughout the figures and the description below, like numerals indicate the same element.

DETAILED DESCRIPTION OF THE PREFERRED EMBODIMENTS

Figure 1:
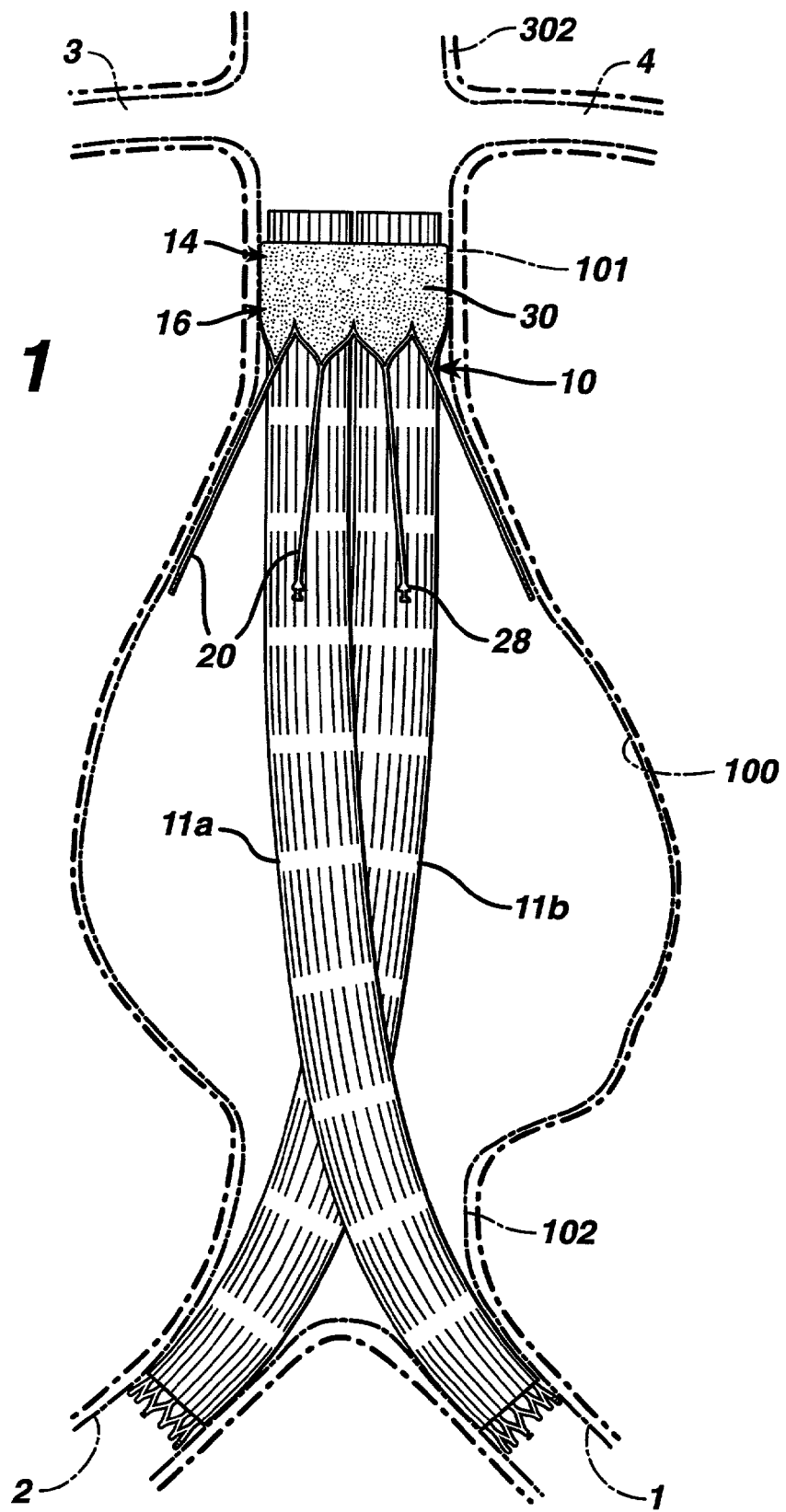
FIG. 1 is an elevation view of a fully deployed aortic repair system for infra-renal use made in accordance with the present invention.

The apparatuses, systems, methods, and kits of the present invention may be used in the treatment of aortic aneurysms, preferably an abdominal aortic aneurysm, among other uses noted below. A better understanding of the present invention and its use in treating aortic aneurysms will be achieved by reading the following description in conjunction with the above-incorporated references.

The present invention is directed to a prosthesis for repairing or bypassing an aneurysm, the prosthesis comprising a gasket material engaging a stent, the stent comprising at least one proximally extending anchor for positioning and/or anchoring the stent in a portion of an artery upstream of the aneurysm, typically a section of healthy tissue. In some exemplary embodiments of the invention, the proximally extending anchor is configured into a lattice or matrix of interconnected struts. In other exemplary embodiments of the invention, the lattice or matrix includes diamond shaped structures. A portion of the matrix may or may not include graft material engaging the matrix.

The present invention is directed to a prosthesis for repairing or bypassing an aneurysm, the prosthesis comprising a graft material engaging a stent, the stent comprising interconnected struts, wherein the stent includes at least one proximally extending strut for positioning the stent in a portion of an artery upstream of the aneurysm. In some exemplary embodiments of the invention, the stent includes a number of proximally extending struts. In the exemplary embodiments of the invention, the proximally extending struts engage or form a matrix of interconnected struts, preferably interconnected struts formed into one or more diamond configurations. A portion of the matrix may or may not include graft material engaging the matrix.

The present invention is also directed to a prosthesis for repairing or bypassing an aneurysm, the prosthesis comprising a graft material engaging a stent, the stent comprising a first matrix of interconnected struts configured to engage a proximal section of an artery, and a second matrix of interconnected struts configured to engage a distal section of the artery, the stent including an intermediate portion comprising at least one longitudinally extending strut connecting the first matrix to the second matrix. A portion of the first matrix and/or the second matrix may or may not include graft material engaging the respective matrix.

The present invention also includes a first prosthesis adapted to engage or seat at least one second prosthesis, the first prosthesis comprising a stent; the stent comprising a first portion suitable for engaging a section of a first artery downstream of a junction between a first artery and a second artery; the stent comprising a second portion suitable for engaging an upstream portion of the first artery, the second portion being adapted to engage a section of the first artery upstream of the junction between the first and second arteries; the stent including elongated struts interconnecting the first portion with the second portion.

The present invention may also include a first prosthesis for repairing or bypassing an aneurysm, the first prosthesis comprising a gasket material engaging a stent, the stent comprising a matrix of interconnected struts, the first prosthesis being configured to engage a section of an artery upstream of an aneurysm; wherein a portion of the gasket material is positioned across the fluid flow path, the portion comprising at least one thread or other element defining a predetermined region within the portion, the predetermined region configured to receive at least one second prosthesis, the second prosthesis being configured for establishing a fluid flow channel through the aneurysm. In some embodiments of the invention, the portion includes a first thread defining a first predetermined region configured to receive a first second prosthesis, and a second thread defining a second predetermined region configured to receive a second prosthesis.

The present invention also includes an anchor, stent, or prosthesis as described above, wherein an intermediate portion of the anchor, stent, or prosthesis is configured into a highly flexible bridge, pivot, joint, axis, juncture, hinge, hub or the like.

In exemplary embodiments of the invention, any intermediate portion described above may be open, i.e., freely permits fluid cross flow, or is free of any graft material.

Any of the prostheses or stents described above may form a component or portion of a system or kit for repairing or bypassing an aneurysm.

The present invention is also directed to a system for repairing and/or replacing an aneurysm, said system being variously configured and/or assembled using components described in more detail below. Typical systems according to this aspect of the invention may include one or more first prostheses or a sealing component, one or more second prostheses or a fluid flow component, and, optionally, one or more component receptacles, assemblies, or connectors for matingly engaging one component with another. Preferred embodiments of a system of the present invention include a sealing component matingly engaged to two fluid flow path components.

Any of the prostheses, stents, systems, or kits described above may be incorporated in a method for treating an aneurysm. In preferred embodiments of the invention, the prostheses, stents, systems, or kits are used to treat an aortic aneurysm, even more preferably, an abdominal aortic aneurysm.

A typical method of the present invention includes positioning a first portion of a stent or first prosthesis in a first section of an artery, positioning a second portion of the stent or first prosthesis in a second section of the artery, the second section being upstream of an aneurysm, and engaging at least one second prosthesis with the stent or first prosthesis, the second prosthesis forming a fluid flow path that bypasses the aneurysm. In preferred embodiments of the invention, the method includes anchoring the system using the second prosthesis in its expanded configuration. The method may further include anchoring the most upstream portion of the system using the first portion of the stent, matrix, or first prosthesis.

The present invention is also directed to a kit that includes one or more of the following: a sterile or sterilizable enclosure; a first prosthesis; a first prosthesis in an individual sterile enclosure; a second prosthesis; a second prosthesis in an individual sterile enclosure; a third prosthesis; a third prosthesis in an individual sterile enclosure; at least one suture; at least one staple; a collar or catheter tip assembly configured to engage and deliver a first prosthesis, a second prosthesis, and/or a third prosthesis; and at least one marker configured for placement on a first prosthesis, a second prosthesis, a third prosthesis, and/or portions thereof.

The present invention also includes a kit comprising a prosthesis according to the invention, preferably in a sterile or sterilizable enclosure.

A system or kit of the present invention may include one or more modular components. As used herein, a modular component is configured, or adapted to engage, or includes one or more structures that are intended to communicate with or engage a complementary structure on another modular component. The present invention also includes a kit that includes one or more of the following: a sterile or sterilizable enclosure; a first prosthesis; a first prosthesis in an individual sterile enclosure; a second prosthesis; a second prosthesis in an individual sterile enclosure; a third prosthesis; a third prosthesis in an individual sterile enclosure; at least one suture; at least one staple; a collar or catheter tip assembly configured to engage and deliver a first prosthesis, a second prosthesis, and/or a third prosthesis; and at least one marker configured for placement on a first prosthesis, a second prosthesis, a third prosthesis, and/or portions thereof.

Embodiments of the invention may further include one or more bypass prostheses configured to matingly engage a first prosthesis, the bypass prosthesis comprising a graft material engaging a stent, the stent comprising a hollow matrix including a series of interconnected struts, the matrix being moveable from a first closed position to a second open position; the stent having at least one attachment structure or connector for matingly engaging at least one second complementary structure on the first prosthesis. In some exemplary embodiments of the invention, the prosthesis further comprises at least one marker. In preferred embodiments of the invention, the marker or markers are positioned on or formed as part of the stent.

Other embodiments of the invention will be evident from the description provided below.

Definitions

As used herein, aortic aneurysm refers to any failure of a conduit, such as an aortic wall, typically characterized by an undesirable dilation of a portion of the artery, vessel malformation, or an occlusion. The system and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. An exemplary use of a system and method of the present invention is to repair an aortic aneurysm, and the use of such term is not intended to limit the use of the structures or systems of the present invention to repair or replace other conduit failures. The prosthesis of the present invention may also be utilized in the thoracic aorta, and may be used to repair thoracic aneurysms or thoracic dissecting aneurysms. Accordingly, use of the term "aortic aneurysm" is intended to relate to and include other aneurysms, including but not limited to both abdominal aortic aneurysms and thoracic aneurysms.

In preferred embodiments of the invention, the system and structures are used to treat, repair, replace, or bypass an abdominal aortic aneurysm.

As used herein fluid pathway refers to any in vivo structure through which a biological fluid passes. A preferred fluid pathway is an artery. Fluid pathways include, but are not limited to channels formed by an artery, a vein, a capillary, lymph nodes and channels, and arteries, veins, and capillaries within an organ or organelle.

As used herein fluid or biological fluid refers to any fluid produced by an animal, including a human. Exemplary biological fluids include but are not limited to blood, oxygenated blood, de-oxygenated blood, gastric fluids, amniotic fluid, spinal fluid, and lymph. The preferred fluid is blood or oxygenated blood.

As used herein, conduit typically refers to any structure used to convey a biological fluid. The conduit may be formed of natural or synthetic materials or combinations thereof. Exemplary conduits include but are not limited to an artery, a vein, a capillary, lymph nodes and channels, and arteries, veins, capillaries within an organ or organelle, and a prosthesis or system according to the invention.

As used herein, "biofusion" is a word coined by assignee referring to the ability of cells, proteins, fibrin, and other biological molecules to incorporate into the pore structure of a material, such as a foam or gasket material, or a graft material. It is believed that this feature promotes a long term stable biological interface that cannot be separated about six weeks after implantation.

The biofusion effect has many advantages. It has the potential to obviate late endo-leakage by preventing areas of non-organized clot from being displaced or recanalized. It is also believed that biofusion creates a connective tissue collar around the prosthesis that may prevent the aortic neck from dilating over time. Restricting neck dilation avoids leakage pathways and implant migration that can be caused by an insufficient fit with the aorta.

As used herein, adapted for communication, communicating, or similar terms refer to any means, structures, or methods for establishing operational association between two elements of the system. Similarly, engaging, adapted to engage, or similar terms refer to means, structures, or methods for contacting a first component, structure, or portion thereof with a second component, structure, or portion thereof. Exemplary structures are shown in the Figures. Typically, all of these terms and phrases refer to at least one structure in or on a first component configured to engage a complementary structure in or on a second component, and the use of these inter-engaging features to link a first prosthesis or component with a second prosthesis or component. The engagement or communication may be matingly (e.g., permanent) and/or releasably (e.g., temporary). In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another prosthesis. As used herein, connector refers to any structure used to form a joint or to join itself to another component or portion thereof. These connectors or connections establish a fluid flow path through various elements of the apparatus, assembly, or system. In a preferred embodiment of the invention, the system is intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, e.g., referring to a position farthest from the beginning; in human anatomy, this term is commonly equivalent to caudal or inferior. Proximal is used in accordance with its ordinary dictionary definition, e.g., referring to a position nearest the beginning; in human anatomy, this term is commonly equivalent to cranial or superior. The terms distal and proximal are intended to convey opposite ends or portions of a device, channel, element, or structure. In relation to a fluid flow path, distal will typically refer to a downstream location in'the fluid flow path, and proximal will typically refer to an upstream location, unless otherwise specifically noted. Anatomically, distal generally refers to "away from the heart" and proximal generally refers to "toward the heart."

A system for treating an aortic aneurysm according to the present invention typically includes a first prosthesis or precursor stent and at least one second prosthesis. In preferred embodiments of the invention, the components of the system are delivered intraluminally to the site of the aneurysm using a catheter or the like. One skilled in the art will therefore recognize that it is beneficial to deliver the components of the system in a closed or first position, and to deploy the component in its functional location by expanding the component into an open or second position.

Figure 11:
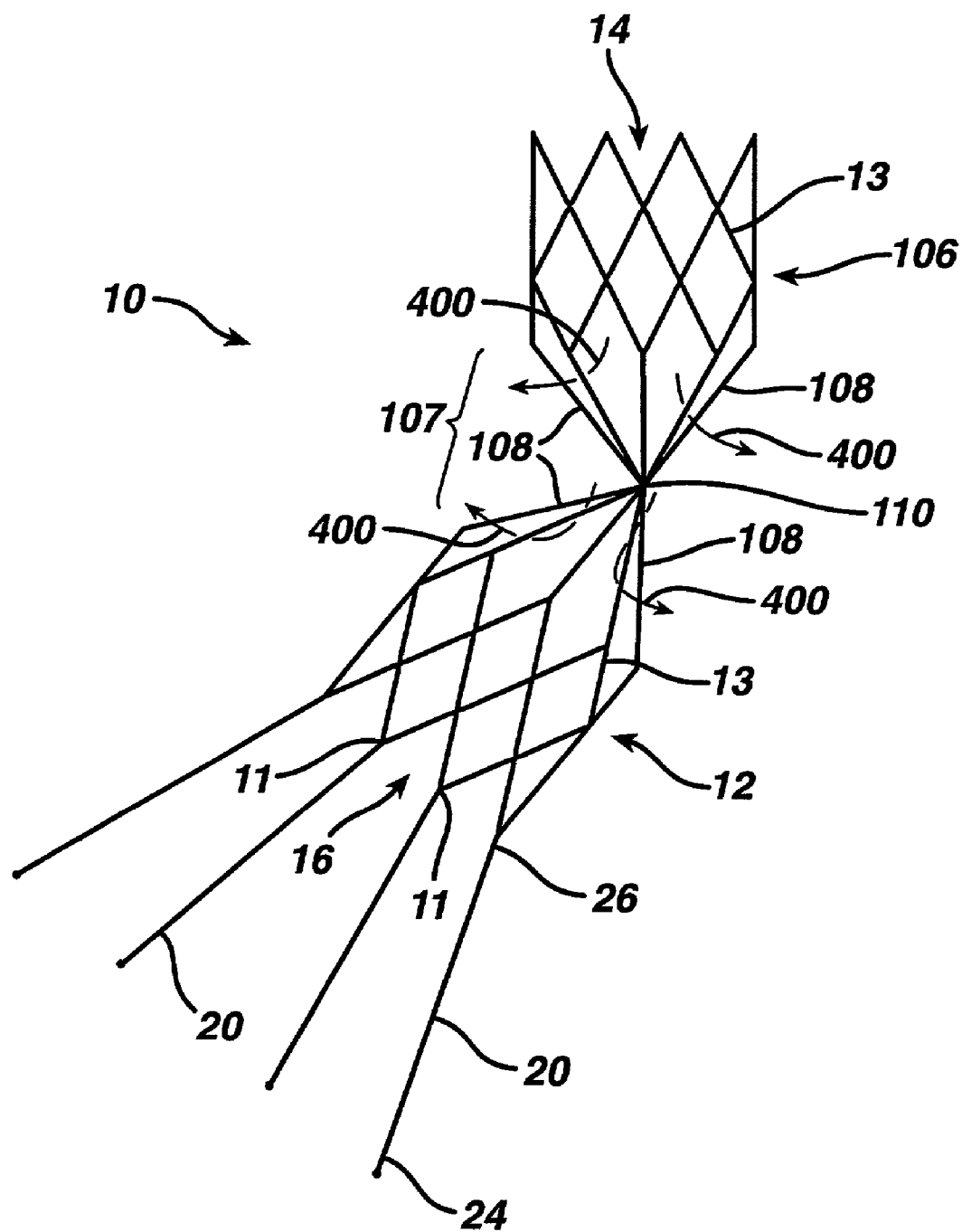
FIG. 11 is a side elevation of an exemplary embodiment of a supra-renal stent of the present invention having an angled or jointed proximal extension anchor.

Jointed stent, as used herein, refers to any stent structure or configuration that permits one section of the stent to be angled in relation to another section. The angled configuration may be fixed or moveable, flexible or non-flexible, preferably to accommodate the angle of the artery in which the prosthesis is placed. An exemplary embodiment is shown in FIG. 11. Although the angle may be any angle, the preferred stent and first prosthesis of the present invention is capable of achieving a greater than about a forty-five degree angle between the two sections. A flexible stent structure, wherein the flexibility is derived from the bridge and/or strut configuration itself, may provide sufficient flexibility and/or articulation to accommodate extreme angulations in an artery's shape. These various flexible stent structures are also included in the meaning of jointed stent.

Each of the components of the system will now be described in more detail. Any references to the figures will be used to illustrate one or more exemplary embodiments of the invention, without intending to limit the invention thereby.

System

Figure 8:
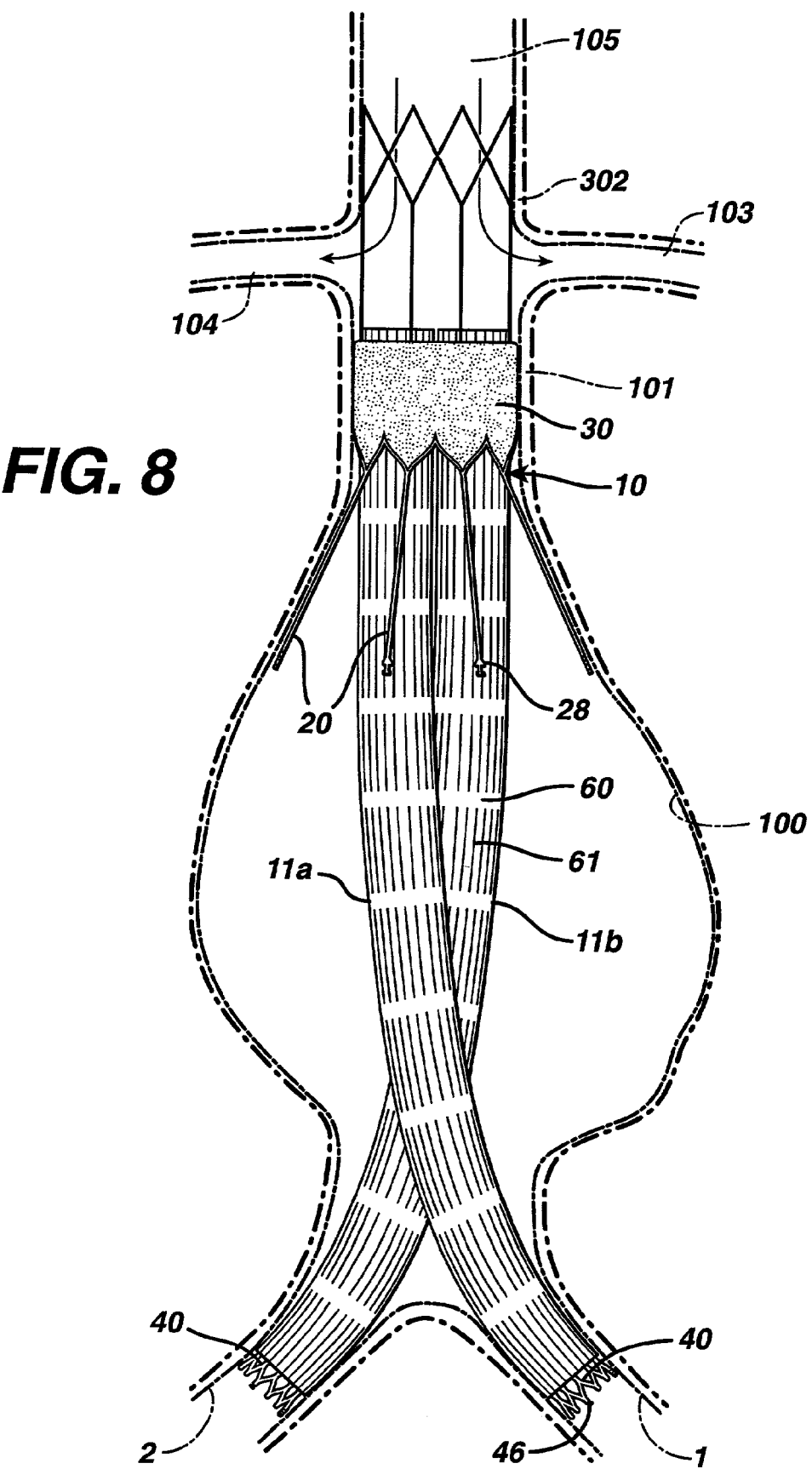
FIG. 8 is an elevation view of an exemplary embodiment of a fully deployed supra-renal aortic repair system of the present invention configured with a proximal extension anchor.

An infra-renal and supra-renal system according to the present invention may include one or more prostheses. Exemplary infra-renal and supra-renal systems are shown in FIGS. 1 and 8 respectively. The system includes a first prosthesis 10 and two second prostheses 11a and 11b, which, in combination, bypass an aneurysm 100. In exemplary embodiments of the invention, a proximal portion of the system may be positioned in a section 101 of an artery upstream of the aneurysm 100, and a distal portion of the system may be positioned in a downstream section 102 of the artery or a different artery.

Figure 9:
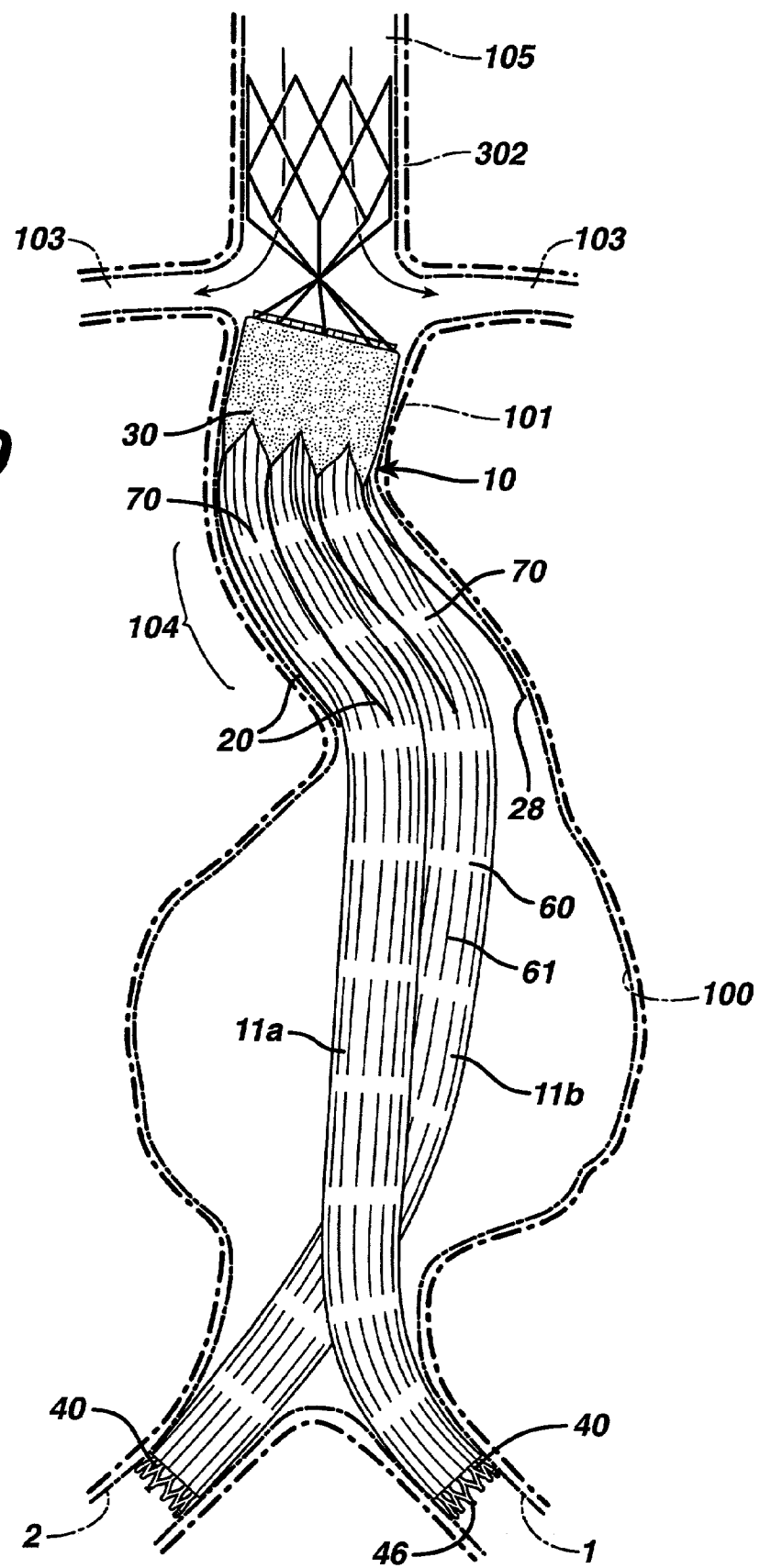
FIG. 9 is an elevation view of an exemplary embodiment of a fully deployed supra-renal aortic repair system of the present invention configured for use in a high angle fluid flow path.
Figure 10:
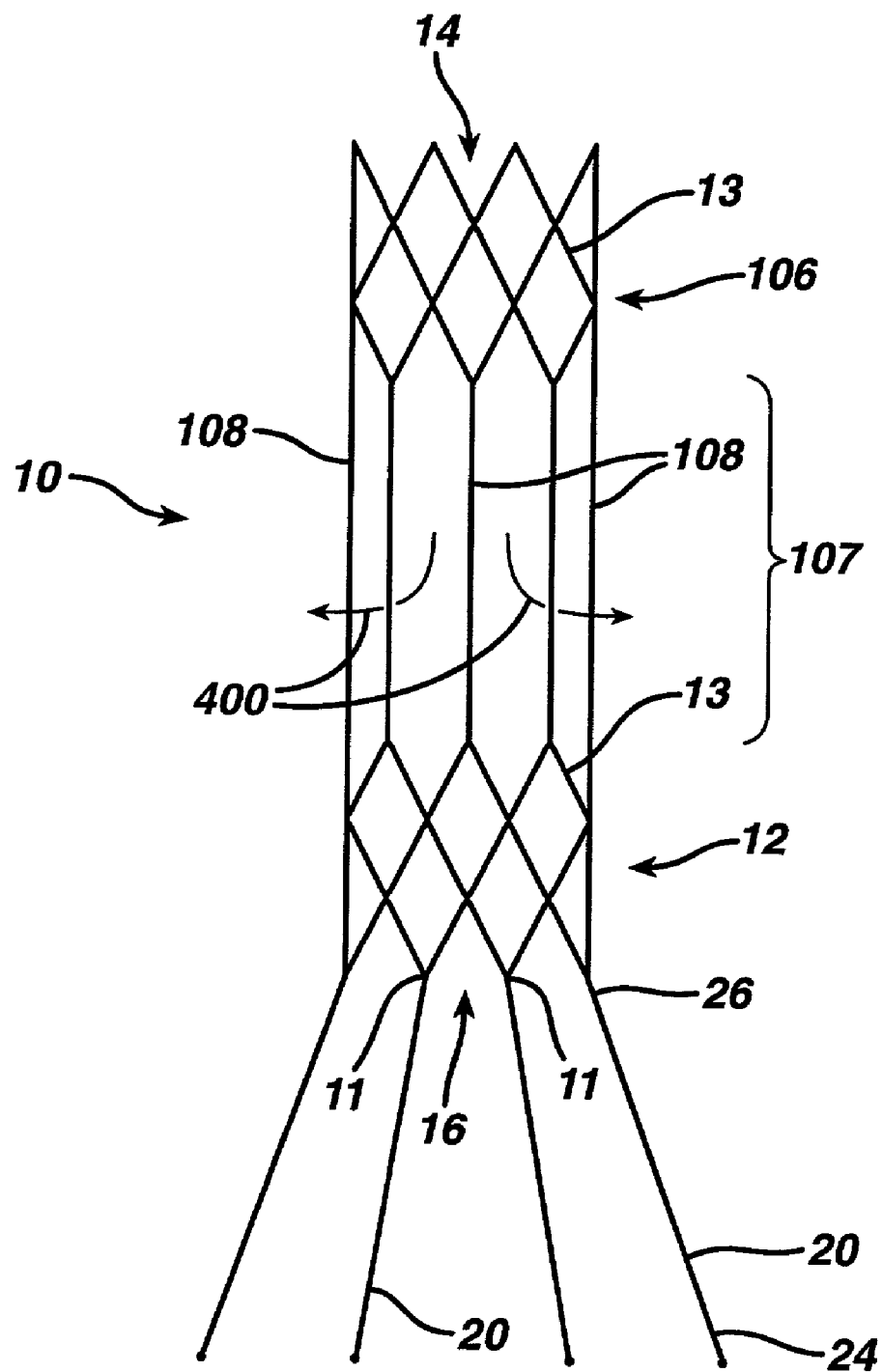
FIG. 10 is a side elevation of an exemplary embodiment of a supra-renal stent of the present invention having a proximal extension anchor.

As shown most clearly in FIG. 9, the system of the present invention is intended for use when section 101 of the artery is unsuitable for anchoring a portion of the system. As noted above, these circumstances exist when the length of section 101 is diseased, too short, includes a junction with a second artery 103, and/or includes one or more angled sections 104 of artery.

Under these and other circumstances, it may be desirable to provide a system, first prosthesis, or stent having a proximal portion that extends into an upstream portion 105 of the artery. This proximal portion anchors the system or prosthesis in a section of the artery that is suitable for engaging and anchoring the system or prosthesis.

A prosthesis of the present invention includes a support, stent, or lattice of interconnected struts defining an interior space having an open proximal end and an open distal end. The lattice also defines an interior surface and an exterior surface. The interior and/or exterior surfaces of the lattice, or a portion of the lattice, may be covered by or support at least one covering material, such as a foam or graft material.

As noted in more detail below in relation to specific system components, some prostheses of the present invention may be configured to seal and/or anchor the system in place, and/or to receive and position other prostheses. Typically these prostheses do not themselves define a fluid flow path. Other prostheses may be configured to define at least one fluid flow path. Typically, these prostheses define a channel or the like through which fluid, such as blood, flows. This channel or fluid flow path typically begins upstream of, or in an upstream portion of, a component of the system. In some embodiments of the invention, the fluid flow path bypasses the aneurysm.

Figure 6:
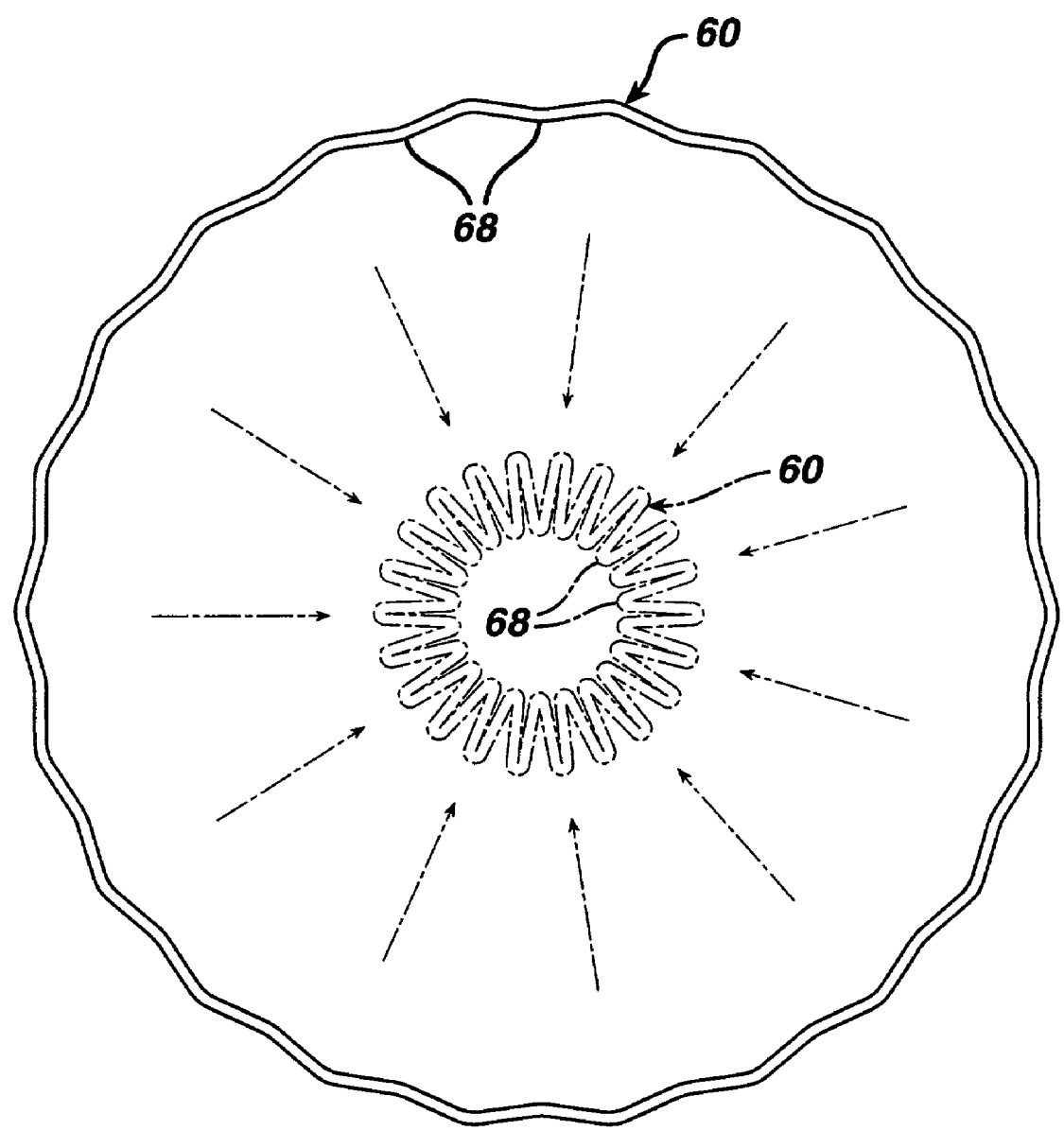
FIG. 6 is an end view of the graft material illustrating the graft material in its unexpanded or crimped configuration, and in its fully expanded configuration.

In some exemplary embodiments of the invention, a prosthesis is moveable between an expanded or inflated position and an unexpanded or deflated position, and any position therebetween. An exemplary embodiment of this feature of the invention is shown in FIG. 6. In some exemplary embodiments of the invention, it may be desirable to provide a prosthesis that moves only from fully collapsed to fully expanded. In other exemplary embodiments of the invention, it may be desirable to expand the prosthesis, then collapse or partially collapse the prosthesis. Such capability is beneficial to the surgeon to properly position or re-position the prosthesis. In accordance with the present invention, the prosthesis may be self-expanding, or may be expandable using an inflatable device, such as a balloon or the like. Even further in accordance with the present invention, there is provided a delivery apparatus for a self-expanding prosthesis. The apparatus includes an outer sheath, comprising an elongated tubular member having distal and proximal ends, and an inner shaft located coaxially within the outer sheath, the shaft having a distal end and a proximal end. The distal end of the shaft further including at least two grooves disposed thereon. The flanges of the first prosthesis are configured to releasably engage the grooves of a portion of the delivery device.

Exemplary embodiments of infra and supra-renal systems for treating an abdominal aortic aneurysm according to the present invention are shown in FIGS. 1, 8, and 9. For the purpose of the infra-renal embodiment, the system is deployed in the infrarenal neck 101 of the abdominal aorta, upstream of where the artery splits into right and left common iliac arteries (also known as first and second iliac arteries). FIG. 1 shows a stent gasket 10 positioned in the infrarenal neck 101; two prostheses, 11a and 11b, the proximal ends of which matingly engage a proximal portion 14 of stent gasket 10, and the distal ends of which extend into an iliac artery 1 or 2. As illustrated, the body of the prosthesis forms a conduit or fluid flow path that passes through the location of the aneurysm 100. In some exemplary preferred embodiments of the invention, the components of the system define a fluid flow path that bypasses the section of the artery where the aneurysm is located. In the supra-renal systems, an anchoring portion may be positioned in healthy tissue above cross-arteries and a sealing portion below the cross-arteries as illustrated in FIGS. 8 and 9.

These and other features of the prosthetic devices and systems of the present invention will be described in more detail below.

First Prosthesis or Sealing Prosthesis

The first prosthesis includes a support matrix or stent that supports a sealing material or foam, at least a portion of which is positioned across a biological fluid flow path, e.g., across a blood flow path. In some exemplary preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed from a wide variety of materials, may be configured in a wide variety of shapes, and their shapes and uses are well known in the art. Exemplary prior art stents are disclosed in U.S. Pat. No. 4,733,665 (Palmaz); U.S. Pat. No.

4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the shape may be generally cylindrical, elliptic, oval, rectangular, triangular, or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials are composed of a biodurable and biocompatible material, including but are not limited to, open cell foam materials and closed cell foam materials. Exemplary materials include polyurethane, polyethylene, polytetrafluroethylene; and other various polymer materials, preferably woven or knitted, that provide a flexible structure, such as Dacron®. Highly compressible foams are particularly preferred, preferably to keep the crimped profile low for better delivery. The sealing material or foam is preferably substantially impervious to blood when in a compressed state.

The sealing material may cover one or more surfaces of the stent i.e., may be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In some exemplary embodiments of the invention, the sealing material stretches or covers a portion of the proximal end of the stent and along at least a portion of the outside wall of the stent.

In some exemplary embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some exemplary embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In exemplary embodiments of the invention, the sealing material is a foam cover that has a single hole.

The sealing material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing prosthesis may be deployed within the infrarenal neck, between an abdominal aortic aneurysm and the renal arteries of a patient, to assist in repairing an abdominal aortic aneurysm.

Figure 2:
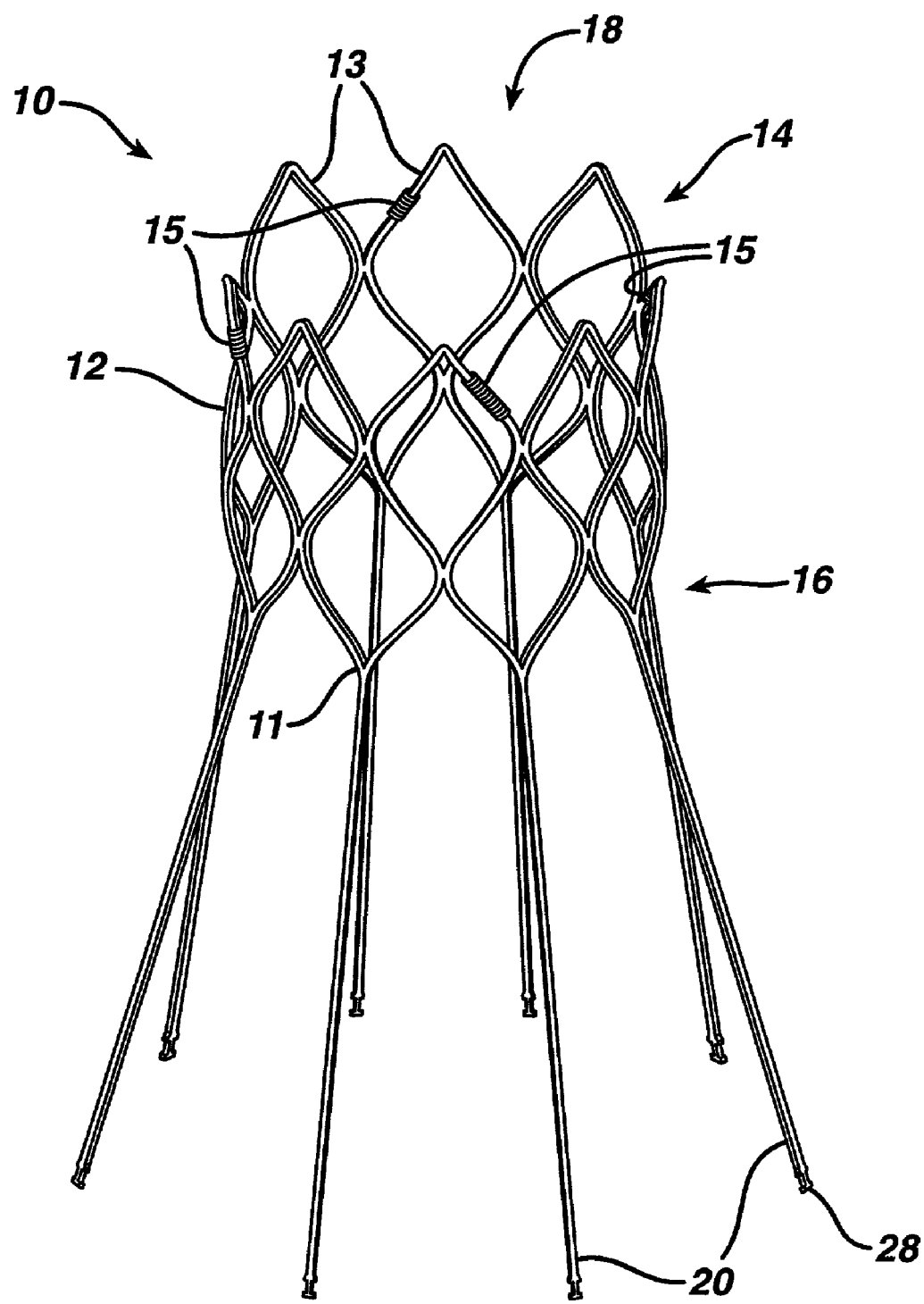
FIG. 2 is a perspective view of a stent for a infra-renal first prosthesis, shown for clarity in an expanded state.
Figure 3:
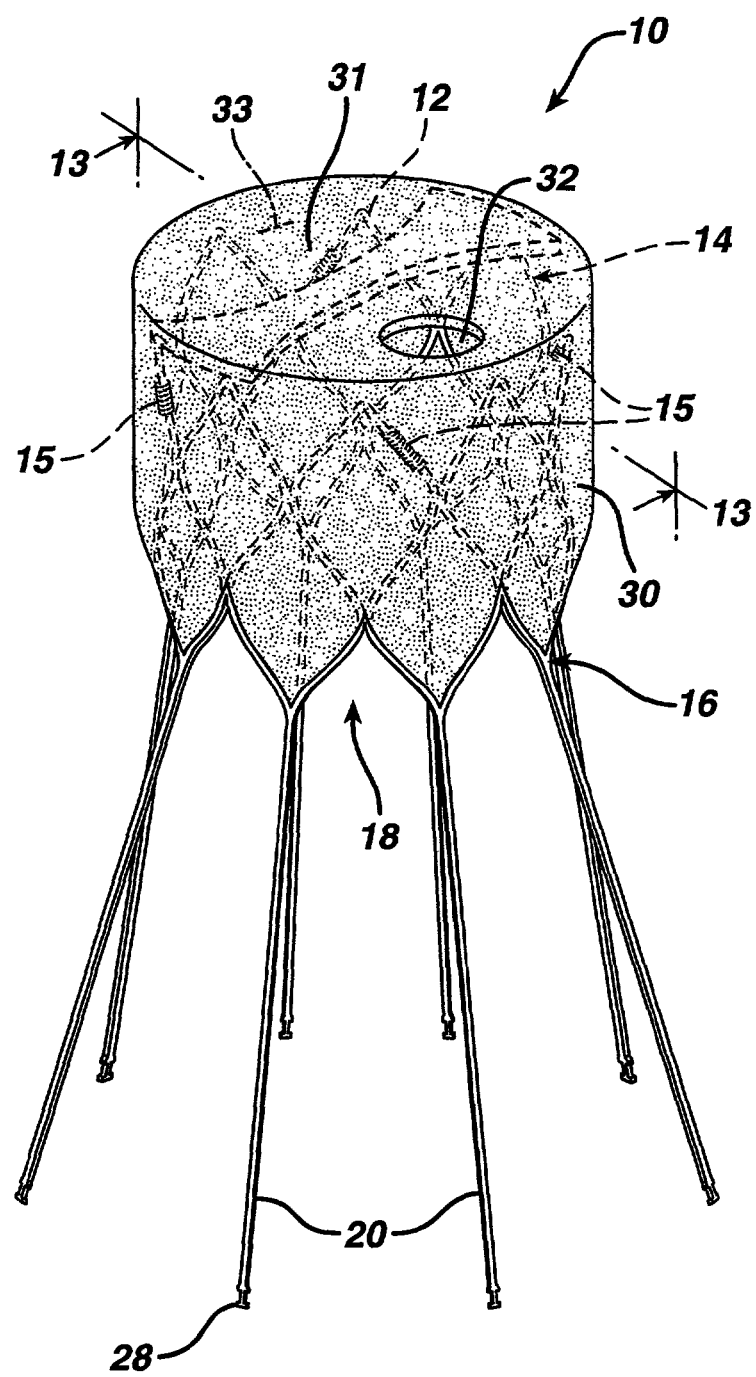
FIG. 3 is a perspective view of a infra-renal first prosthesis having a stent covered by a gasket material.

FIGS. 1-3 show an exemplary infra-renal sealing prosthesis 10 of the present invention. Sealing prosthesis 10 includes a cylindrical or oval cross-sectional self-expanding lattice, support, or stent 12, typically made from a plurality of interconnected struts 13. Stent 12 defines an interior space or lumen 18 having two open ends, a proximal end 14 and a distal end 16. One or more markers may be optionally disposed in or on the stent between the proximal end 14 and the distal end 16.

Stent 12 may further include at least two, but preferably eight (as shown in FIG. 2), spaced apart longitudinal legs 20. Preferably, there is a leg extending from each apex 11 of diamonds formed by struts 13. At least one leg, but preferably each leg, includes a flange 28 adjacent its distal end which, as is described in greater detail below, allows for the stent to be retrievable into its delivery apparatus after partial or nearly full deployment of stent 12 so that it may be turned, or otherwise repositioned for proper alignment.

FIG. 3 shows the sealing material 30 covering the proximal end of stent gasket 10. In the exemplary embodiment shown in FIG. 3, sealing prosthesis 10 includes a sealing material 30 having a first opening or hole 32 and a second opening or slit 33.

The gasket or sealing material covers at least a portion of the interior or exterior of the stent, and most preferably covers substantially all of the exterior of the stent. For example, gasket material 30 may be configured to cover stent 12 from the proximal end 16 to the distal end 14, but preferably not covering longitudinal legs 20.

The sealing material helps impede any blood trying to flow around bypass prostheses 11a and 11b after they have been deployed (as shown in FIG. 1), and from flowing around the stent gasket itself. For this exemplary embodiment, sealing material 30 is a compressible member or gasket located along the exterior of the stent 12 and at least a portion of the interior of the stent 12.

Figure 13:
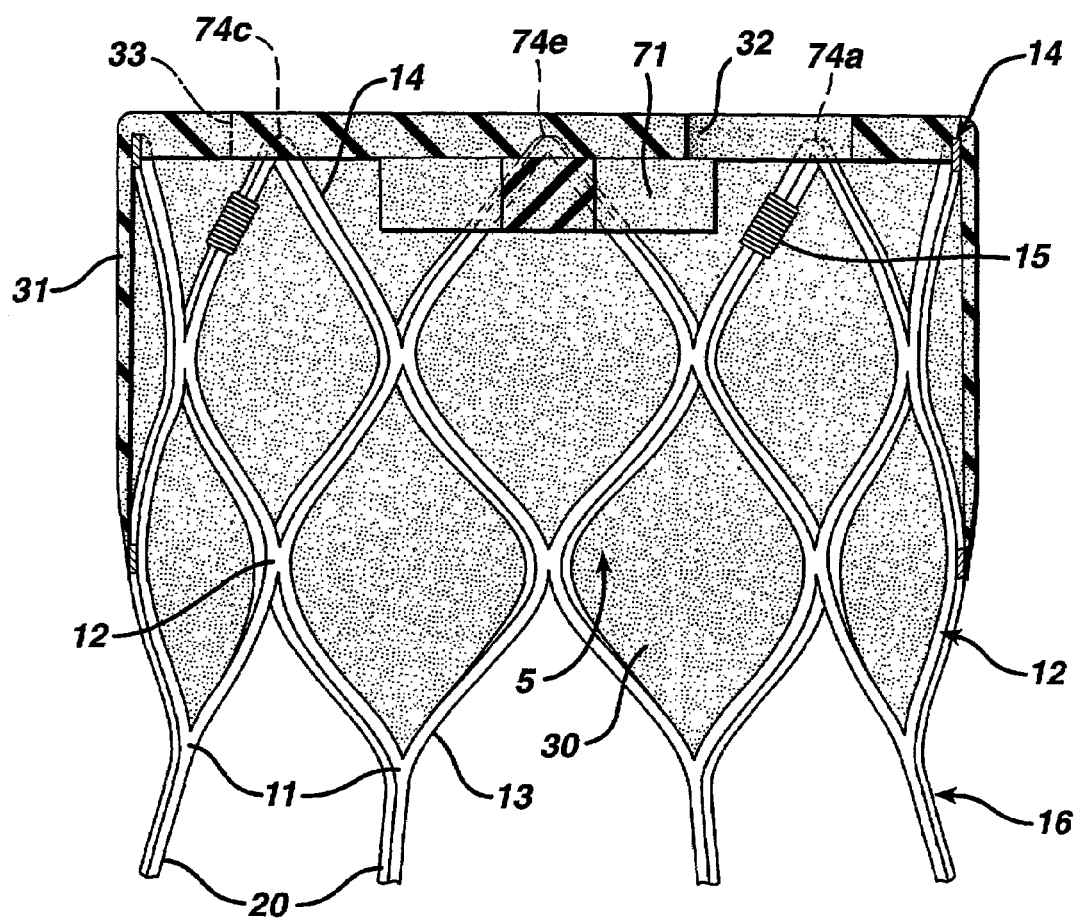
FIG. 13 is a side cross section of a first infra-renal prosthesis according to the present invention.

Exemplary embodiments of the invention are illustrated in FIGS. 13 and 14(a-c). These Figures show a first prosthesis 10 having a gasket material 30 that covers at least a portion of the proximal end of the first prosthesis 10. The gasket material 30 preferably includes a partition that extends approximately across the diameter of the cross section of the first prosthesis 10, wherein the partition includes a thicker gasket material, or further includes a foam or the like. The partition may be formed from any of the gasket or foam materials described above.

The exemplary embodiments illustrated in FIGS. 13 and 14 include a thicker partition 71 in roughly an hourglass shape, although other shapes and sizes may be used. The partition defines at least one section 72 within the prosthesis having less material or the like, these sections being configured for receiving a proximal end of a second prosthesis, as is described in more detail below. In the exemplary embodiments shown in FIGS. 14(a-c), partition 71 defines a first section 72a and a second section 72b; first section 72a is configured to receive a first second prosthesis 11a, and second section 72b is configured to receive a second prosthesis 11b, as described below.

In accordance with the present invention, it may be desirable to include one or more fibers, threads, filaments, straps, or the like for further defining a section 72. In the description below, the word fiber will be used as a shorthand descriptor for the element that includes fibers, threads, filaments, straps, or the like. In preferred embodiments of the invention, the fiber, etc., assists in positioning a second prosthesis 11a or b.

In accordance with the present invention, the fiber or thread may be formed from any material and/or comprise any construction suitable for use in a biological environment, e.g., suitable for use in a blood vessel. The fiber may be woven or non-woven, formed of a synthetic or natural material, and/or single or multi-filament. Exemplary materials for forming the fiber or thread include but are not limited to polyester, Dacron®, Teflon®, polyurethane, porous polyurethane, expanded polyurethane, silicone, polyethylene terephthalate, and expanded polytetrafluoroethylene (ePTFE). The fiber or thread may also take on other forms. For example, the fiber or thread may be formed from glues or adhesives, or by melting sections of the gasket material. In addition, the fiber or thread may comprise struts deformed out of the circumferential plane.

The end or ends of the fiber may be unattached or attached. In a preferred embodiment of the invention, both ends of the fiber are attached or fixed. For example, the ends may be sewn or fixed to the cover 31. In a preferred embodiment of the invention, the ends of the fiber are fixed to a strut 13, even more preferably to a proximal portion of stent 12. One or more ends of the fiber may be fixed to the stent 12 or the strut 13 by threading, knotting, sewing, with adhesives, or any other mechanism for fixing the end of the fiber in place.

Figure 14A:
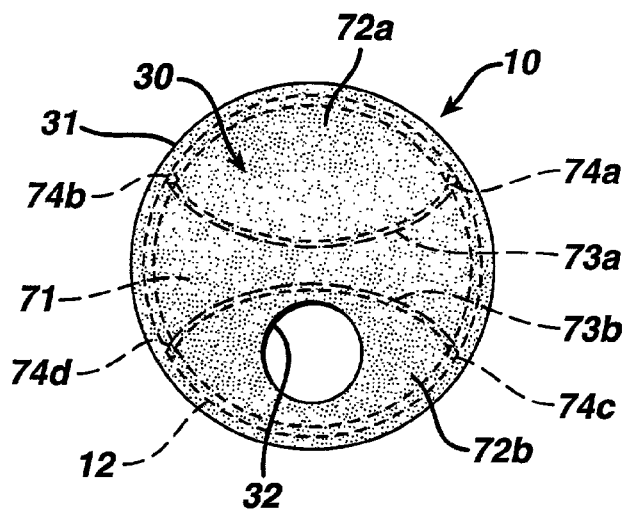
FIGS. 14(a-c) are a top view of alternate exemplary embodiments of a cover on a first infra-renal prosthesis according to the present invention.
Figure 14B:
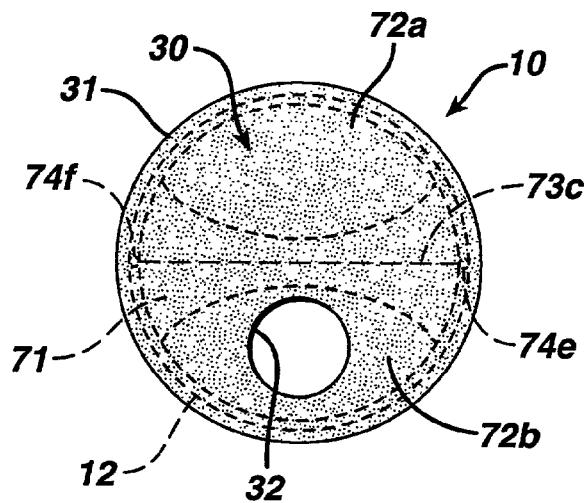
Figure 14C:
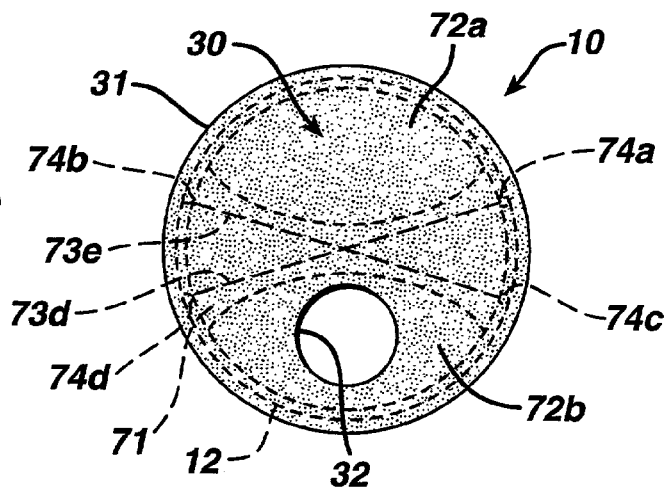

In the exemplary embodiments of the invention illustrated in FIGS. 14 (a-c), fiber 73 may be variously configured. In FIG. 14a, fibers 73a and 73b may be interwoven in the cover 31, and define or form first section 72a and a second section 72b, as noted above. As shown, the ends of the fibers may be fixed to a strut; see 74a, 74b, 74c, and 74d. In FIG. 14b, a single fiber 73c may be positioned across the diameter of the cover 31, and is fixed to a strut at 74e and 74f. In FIG. 14c, one or more crossed fibers 73d and 73e may be used to form or define partitions 72a and 72b respectively. In the illustrated embodiments, the ends may be attached to the stent 12 at 74a, 74b, 74c, and 74d.

In some exemplary embodiments according to the present invention, it may be desirable to use a fiber that is frangible or breakable. In these exemplary embodiments of the invention, the fiber breaks as the unexpanded prosthesis is expanded to its fully deployed position. Alternately, the ends of the fibers may be releasably fixed to the stent or strut when the prosthesis is in a collapsed condition, with one or more ends releasing as the prosthesis expands to its fully deployed position.

These structures promote proper side by side placement of one or more, preferably multiple, prostheses within the first prosthesis 10.

FIGS. 8, 9, 10 and 11 show alternative configurations of a stent 10 intended for use with arterial sections unsuitable for use with a typical stent, such as that shown in FIG. 2. These stents are utilized for supra-renal anchoring. The stent configurations shown in FIGS. 8, 9, 10 and 11 include a first portion or matrix 12 configured to engage a downstream portion of an artery 101 (upstream of an aneurysm), and a second portion or matrix 106 configured to engage an upstream portion of the artery 302. In arterial networks that are configured the same as or similar to the abdominal aorta network illustrated in FIG. 8, matrix 106 may be configured to engage a portion of the artery 302 upstream of a second artery, such as a renal artery 103.

In these exemplary embodiments of the invention, the struts 13 of matrix 12 include a proximally extending bridge 107 comprising at least one elongated strut 108 that communicates with or connects to the matrix 106. The exemplary embodiment of the invention shown in FIG. 10 includes a plurality of struts 108, for example, eight, that in combination form a straight bridge. The exemplary embodiment of the invention shown in FIG. 11 includes a plurality of struts 108, for example, eight, that in combination form a jointed bridge, described in more detail below.

In accordance with the present invention, the upstream portion, component, or prosthesis of the system may be variously configured to achieve a highly flexible structure suitable for accommodating one or more highly angled sections of an artery. In exemplary embodiments of the invention, the flexibility is achieved without creating kinks in the structure. In addition to the exemplary configurations shown in FIGS. 8, 9, 10, 11, 12a-c, the upstream portion, component, or prosthesis of the system may include open or unattached diamonds or struts, resilient struts, or the like as explained in detail subsequently. In certain exemplary embodiments of the invention, the stent or matrix configuration is flexible both longitudinally and radially. As used herein, longitudinal flexibility refers to the ability for a stent or matrix to shorten or elongate as needed.

In the exemplary embodiments of the invention that include a stent configured as those shown in FIGS. 8, 9, 10 and 11, gasket material 30 preferably engages only the first portion 12 of stent 10. Alternately, gasket material 30 may also engage second portion 106 of stent 10. In the certain exemplary embodiments of the invention, bridge 107 is open or allows fluid cross flow, as is depicted by the arrows in FIGS. 8-11. In these exemplary embodiments of the invention, gasket material 30 does not engage bridge 107, or the amount of gasket material that engages bridge 107 does not prevent fluid cross flow. In other exemplary embodiments of the invention (not shown), gasket material 30 engages or covers bridge 107, but in this exemplary embodiment of the invention, the section of gasket material 30 that engages bridge 107 is porous, even more preferably, highly porous. It is intended that these various configurations of the stent and gasket material should not impede or substantially impede the flow of blood through the first prosthesis and into arteries 103.

As noted above, the bridge section interposed between the first matrix 12 and the second matrix 106 may be configured to accommodate a bend or highly angulated portion of an artery. In accordance with the present invention, bridge section 107 may be variously configured to allow a prosthesis to have an angled or flexible conformation. One skilled in the art will readily recognize that the need for a prosthesis having an angled conformation may be dependent on a number of factors, including but not limited to, the specific pathological condition of the patient, the flexibility of a given prosthesis, stent, or assembly, and the purpose for which the prosthesis is being used, among others.

In accordance with the present invention, first matrix 12 and second matrix 106 may comprise similar or the same structures or elements. In some exemplary embodiments of the invention, second matrix 106 may be configured to achieve a greater outwardly radial force to anchor the system against or within the artery. In these exemplary embodiments of the invention, the first matrix 12 may not need to achieve a similar outwardly radial force since this section may receive one or more second prostheses which provide, when expanded or deployed, sufficient outwardly radial force to anchor the system in the artery.

One skilled in the art will also recognize that some of the "straight" embodiments described above may be used in pathological conditions that involve or need an angled blood or fluid flow path. For example, a straight prosthesis may be used when only a small angle is involved. Any of the straight exemplary embodiments described above may be deformed to achieve an angled fluid flow path if the amount of deformation does not adversely affect the function of the prosthesis or the well being of the patient.

Conversely, one skilled in the art will recognize that a pathological or biological condition having a fluid flow path from a slight deflection to a wide angle (e.g., from about forty-five degrees to about ninety degrees) may warrant the use of a prosthesis having a structural configuration or element that allows the prosthesis to achieve the angled configuration. In these situations, it is believed that the following are exemplary embodiments of the invention that would provide beneficial results in achieving a fluid flow path through a tortuous channel.

A prosthesis having an angled configuration may be achieved by interposing one or more flexible struts, flexible diamonds, open diamonds, pivots, joints, axes, junctions, hinges, narrows, hubs, or the like, in the struts 108 or the bridge 107 between matrix 12 and matrix 106. Individual struts 108 may be joined or connected at this joint, as is shown in FIGS. 11, 12a, and 12b, in various configurations that allow a prosthesis or stent to achieve an angled configuration.

In some exemplary embodiments of the invention, an intermediate section of the bridge 107 includes a pivot 120 or hinge. Pivot 120 in FIG. 12c, and similar configurations, allow some degree of movement between the struts of the bridge, i.e., the angles between adjacent struts are moveable or changeable.

Figure 12A:
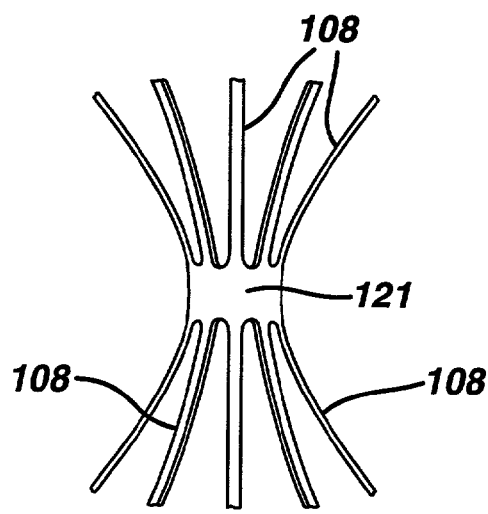
FIGS. 12(a-c) show alternative exemplary embodiments of an angle junction for the stent of FIG. 11.
Figure 12B:
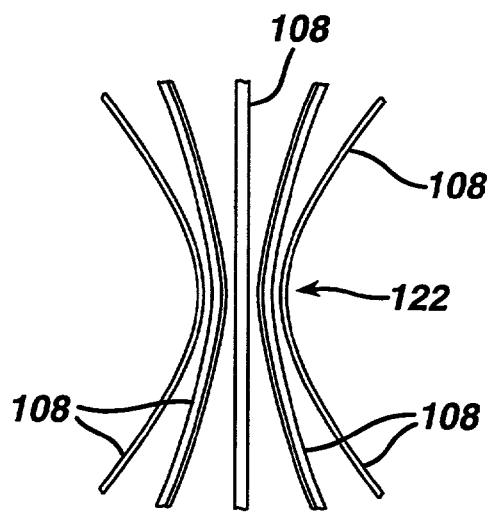
Figure 12C:
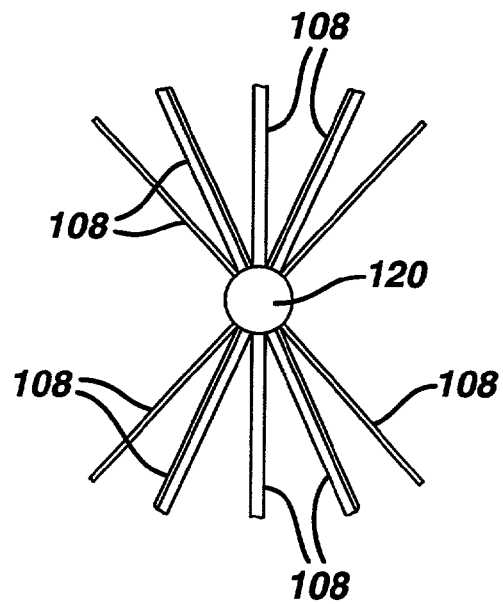

The present invention also includes a prosthesis or stent having an intermediate section of the bridge 107 that comprises a joint, junction, or hub 121 in which the struts are fixed together at the intermediate section as illustrated in FIG. 12a.

The present invention also includes a prosthesis or stent having an intermediate section of the bridge 107 that comprises a narrow or corseted configuration 122 in which a portion of the struts 108 are positioned in close proximity to a portion of another strut. The exemplary embodiment in FIG. 12b shows an intermediate portion of the struts in close proximity to each other.

Figure 15:
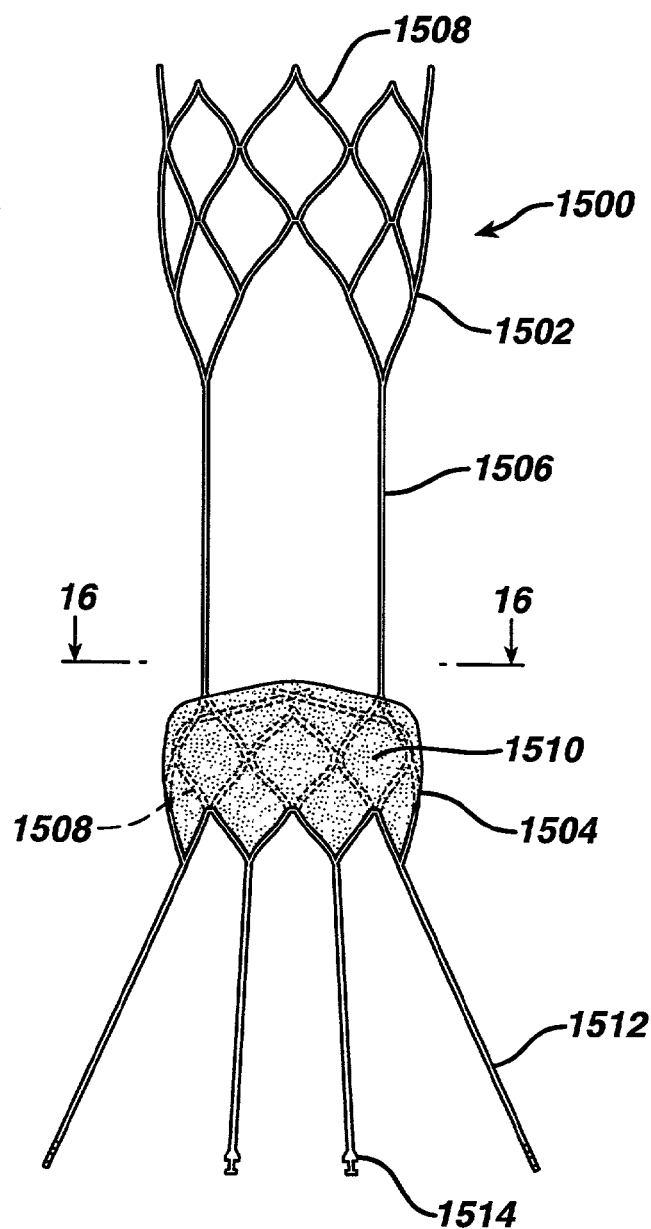
FIG. 15 is a front elevational view of an alternate exemplary embodiment of supra-renal anchoring device in accordance with the present invention.
Figure 16:
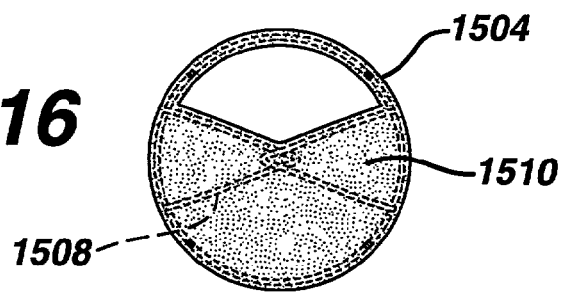
FIG. 16 is a top sectional view of the supra-renal anchoring device of FIG. 15 taken along section line 16-16.

FIG. 15 illustrates an alternate exemplary supra-renal anchoring stent gasket 1500. In this exemplary embodiment, the supra-renal anchoring stent gasket 1500 comprises an anchoring portion 1502 and a sealing and anchoring portion 1504. The anchoring portion anchors the stent gasket 1500 in healthy tissue above cross-arteries, for example, the renal arteries. The sealing and anchoring portion 1504 seals and anchors the second prostheses, described in detail below. The anchoring portion 1502 and the sealing and anchoring portion 1504 are connected by a plurality of struts or bridges 1506 and both portions comprise a plurality of struts 1508 which may be interconnected in any number of suitable geometric patterns such as diamonds. As illustrated in FIG. 16, struts forming the geometric pattern may be deformed out of the circumferential plane towards the center of the lumen to create flaps. The sealing and anchoring portion 1504 is covered with a sealing material or gasket 1510 which serves as a sealing means for the second prostheses. These flaps act similarly to the stitching illustrated in FIGS. 14a-c. As in the other designs, the supra-renal anchoring stent gasket comprises recapture legs 1512 with flanges 1514 as described above.

Figure 17:
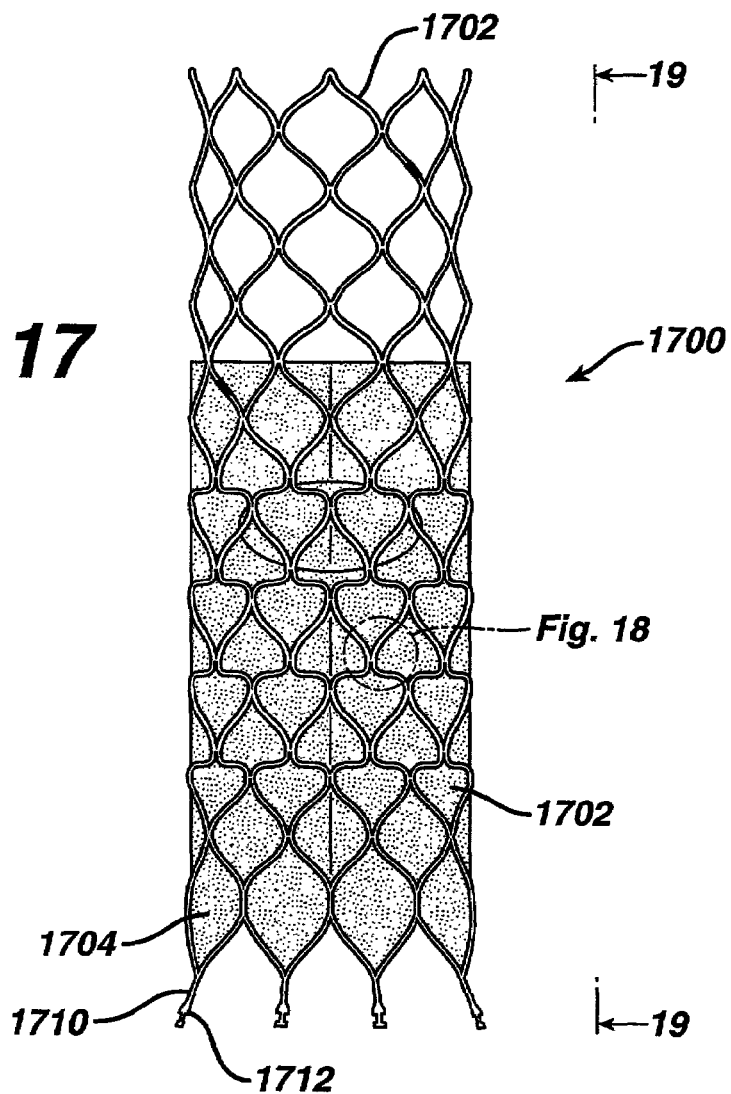
FIG. 17 is a front elevational view of an alternate exemplary embodiment of a supra-renal anchoring device in accordance with the present invention.
Figure 18:
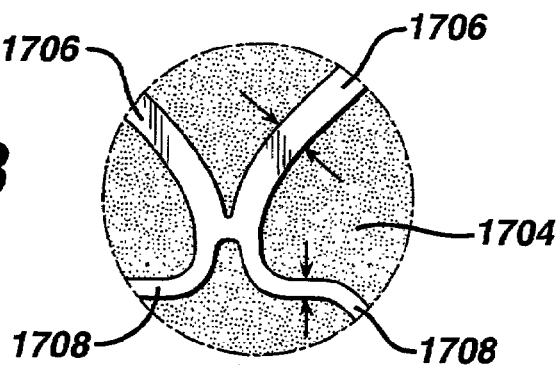
FIG. 18 is an enlarged fragmentary view of a portion of the supra-renal anchoring device of FIG. 17.
Figure 19:
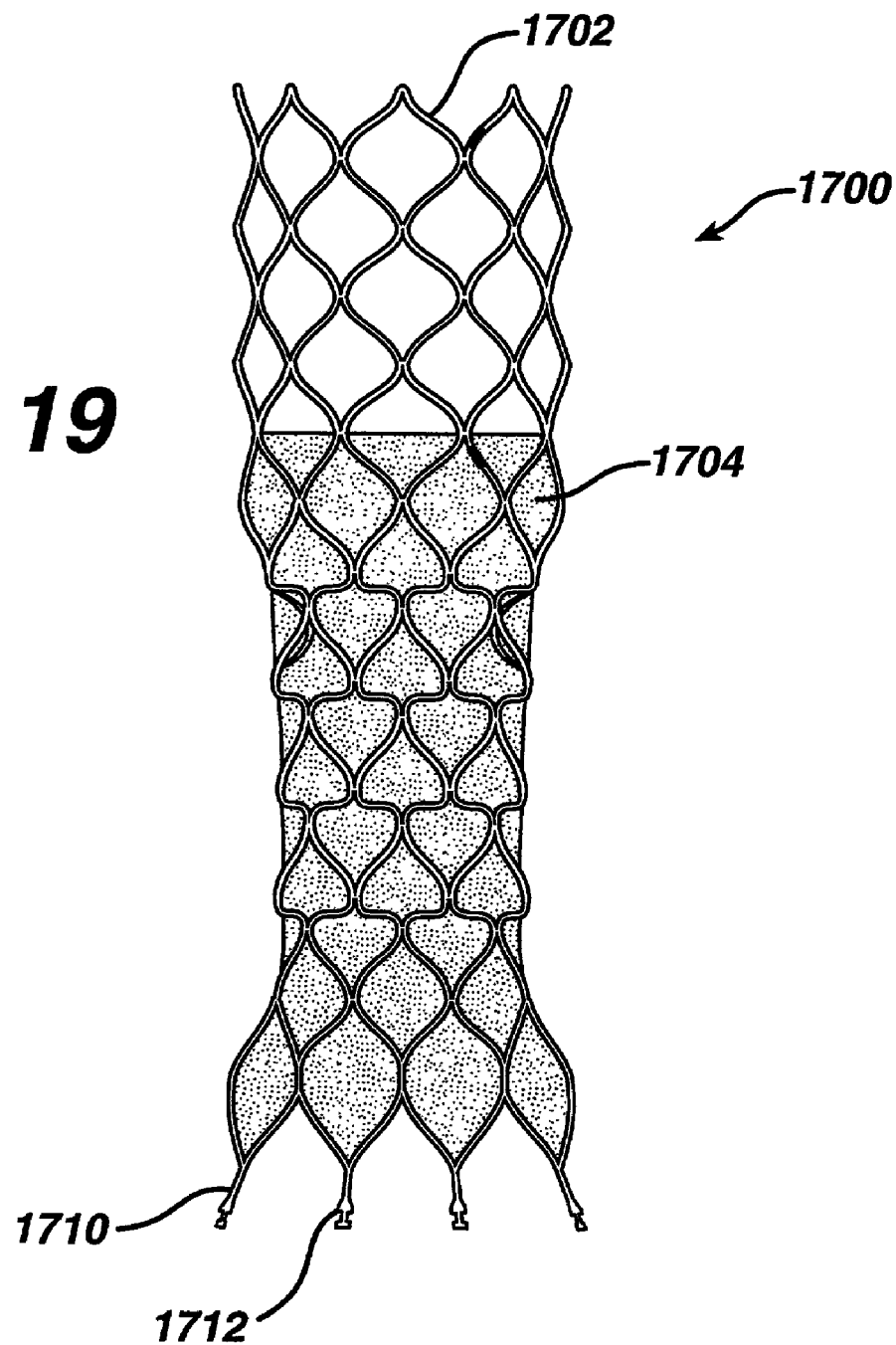
FIG. 19 is a side elevational view of the supra-renal anchoring device of FIG. 17 taken along section line 19-19.
Figure 20:
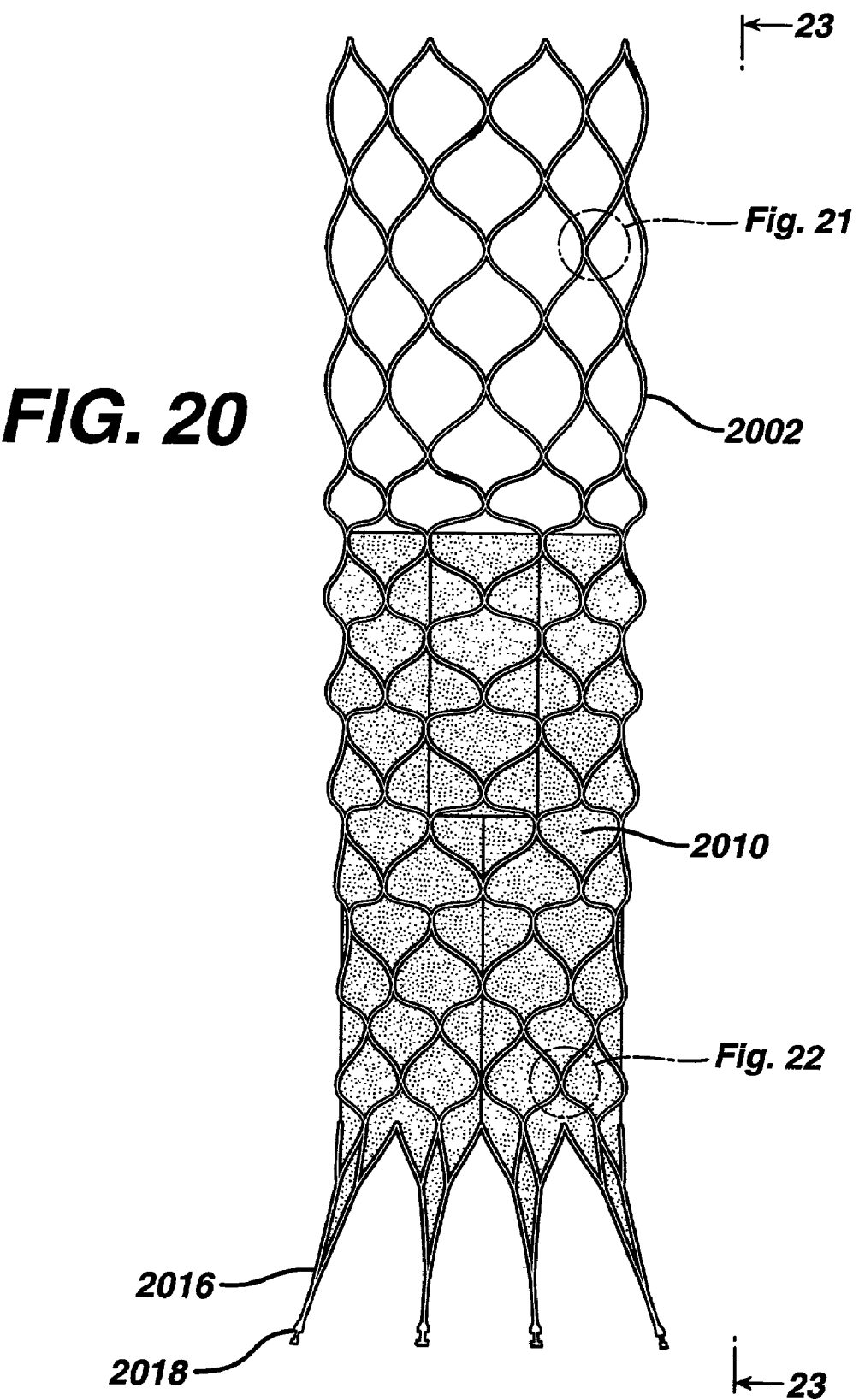
FIG. 20 is a front elevational view of an alternate exemplary embodiment of a supra-renal anchoring device in accordance with the present invention.
Figure 21:
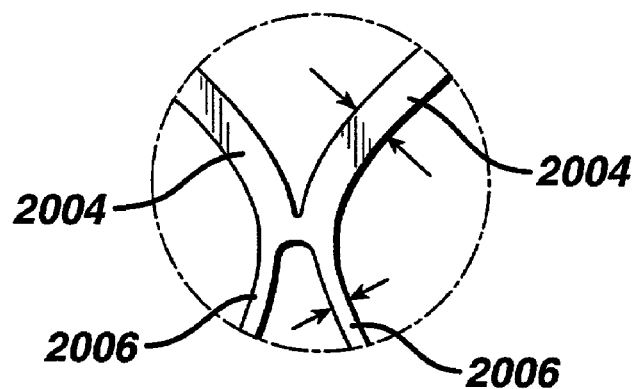
FIG. 21 is an enlarged fragmentary view of a first portion of the supra-renal anchoring device of FIG. 20.

FIGS. 17-19 illustrate yet another alternate exemplary supra-renal anchoring stent gasket 1700. In this exemplary embodiment, the supra-renal anchoring stent gasket 1700 comprises an essentially one piece structure formed into a geometric pattern by a number of interconnected struts 1702. Once again, the geometric pattern may comprise diamond like structures. As described above, a portion of the stent gasket 1700 comprises open space to allow for cross blood flow while another portion comprises a sealing material or gasket 1704. In this exemplary embodiment, the interconnected struts 1702 in the distal sections of the stent gasket 1700 comprise specially configured geometric patterns as illustrated in the detail of FIG. 18. As illustrated in FIG. 18, the upper struts 1706 are thicker than the lower struts 1708. This type of design increases the flexibility of the stent gasket 1700 making it especially advantageous for use in angulated sections or arteries. As before, the stent gasket 1700 comprises recapture legs 1710 and flanges 1712.

Figure 22:
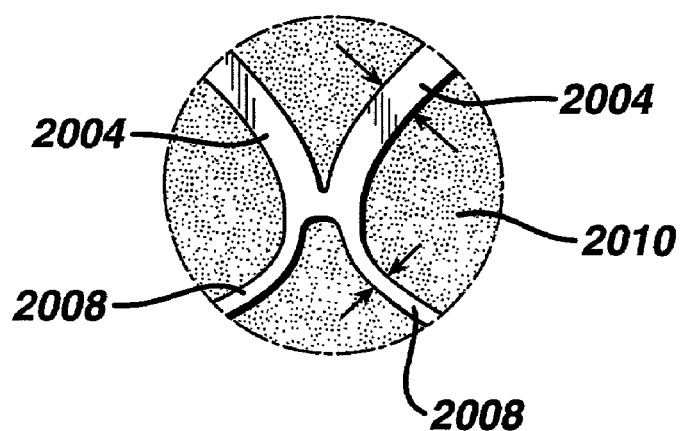
FIG. 22 is an enlarged fragmentary view of a second portion of the supra-renal anchoring device of FIG. 20.
Figure 23:
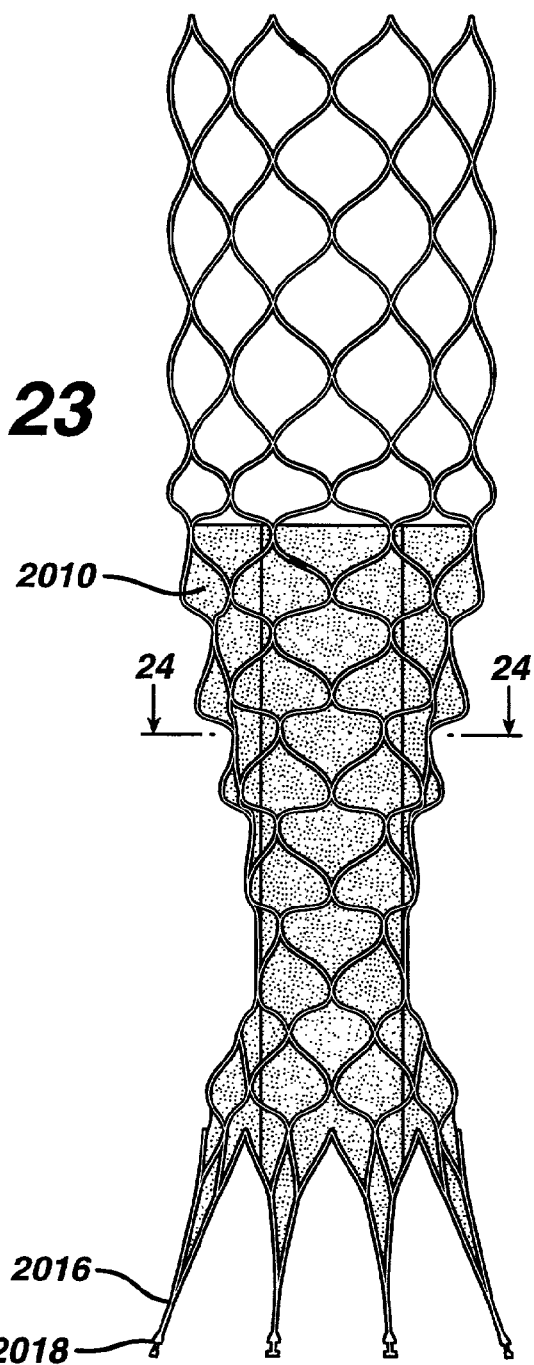
FIG. 23 is a side elevational view of the supra-renal anchoring device of FIG. 20 taken along section line 23-23.
Figure 24:
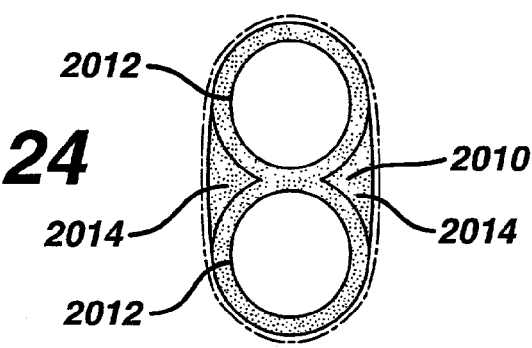
FIG. 24 is a top sectional view of the supra-renal anchoring device of FIG. 23 taken along section line 24-24.
Figure 25:
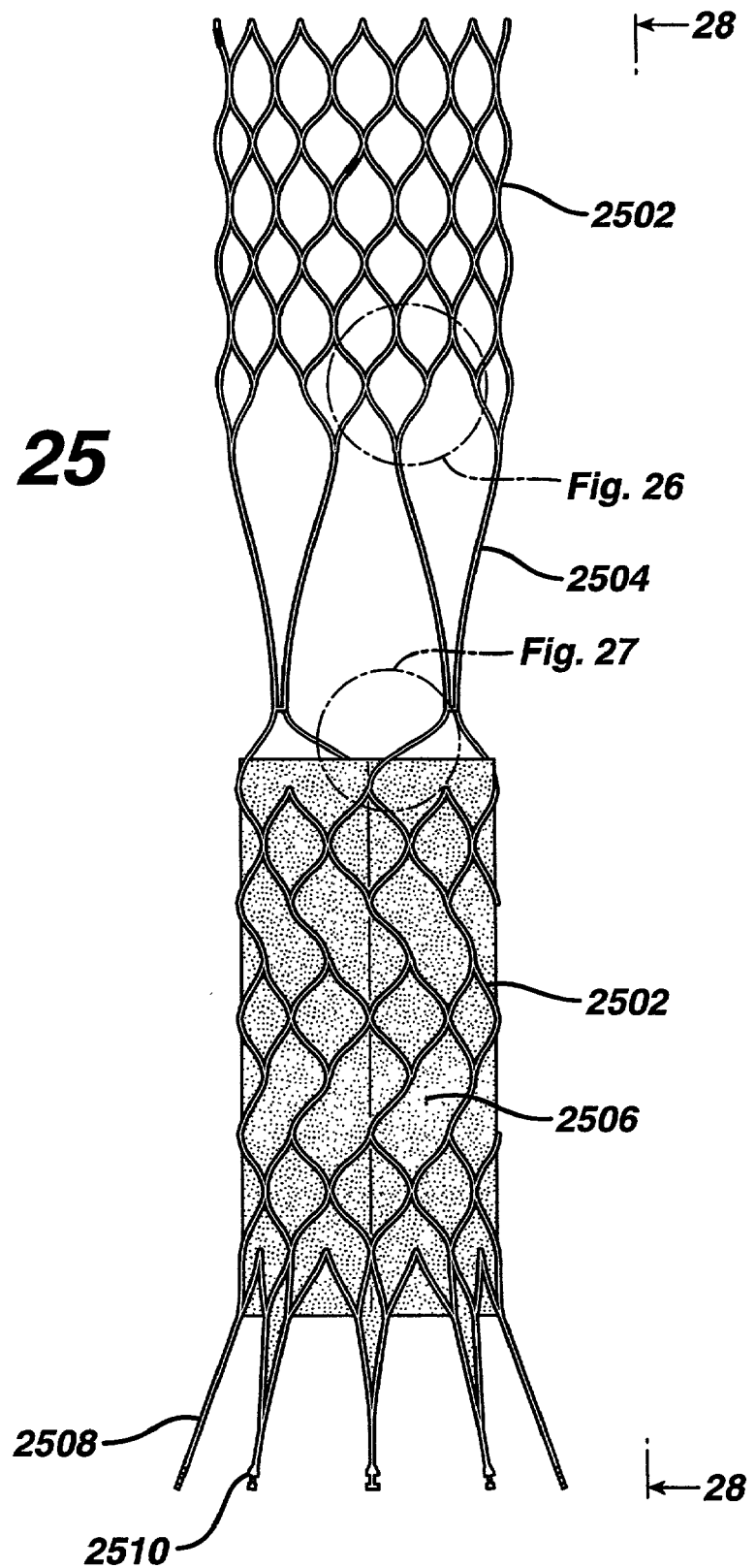
FIG. 25 is a front elevational view of an alternate exemplary embodiment of a supra-renal anchoring device in accordance with the present invention.
Figure 26:
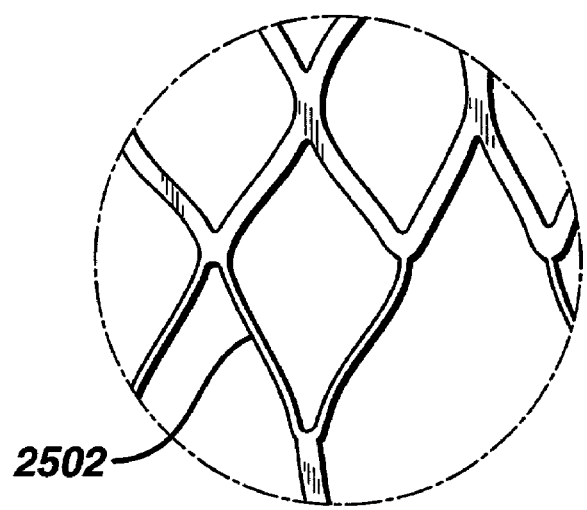
FIG. 26 is an enlarged fragmentary view of a first portion of the supra-renal anchoring device of FIG. 25.
Figure 27:
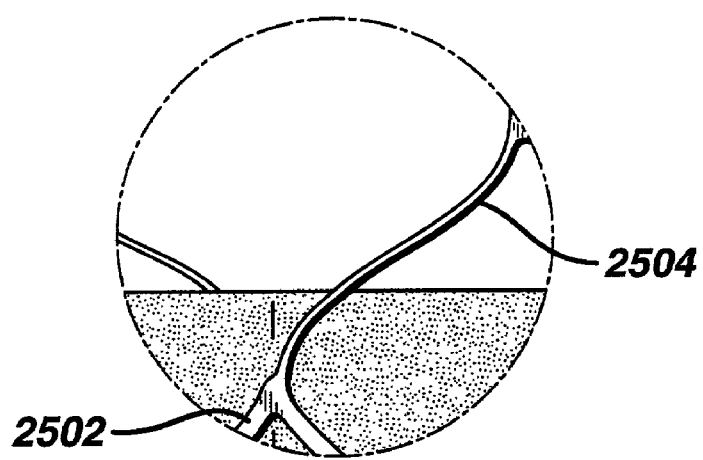
FIG. 27 is an enlarged fragmentary view of a second portion of the supra-renal anchoring device of FIG. 25.
Figure 28:
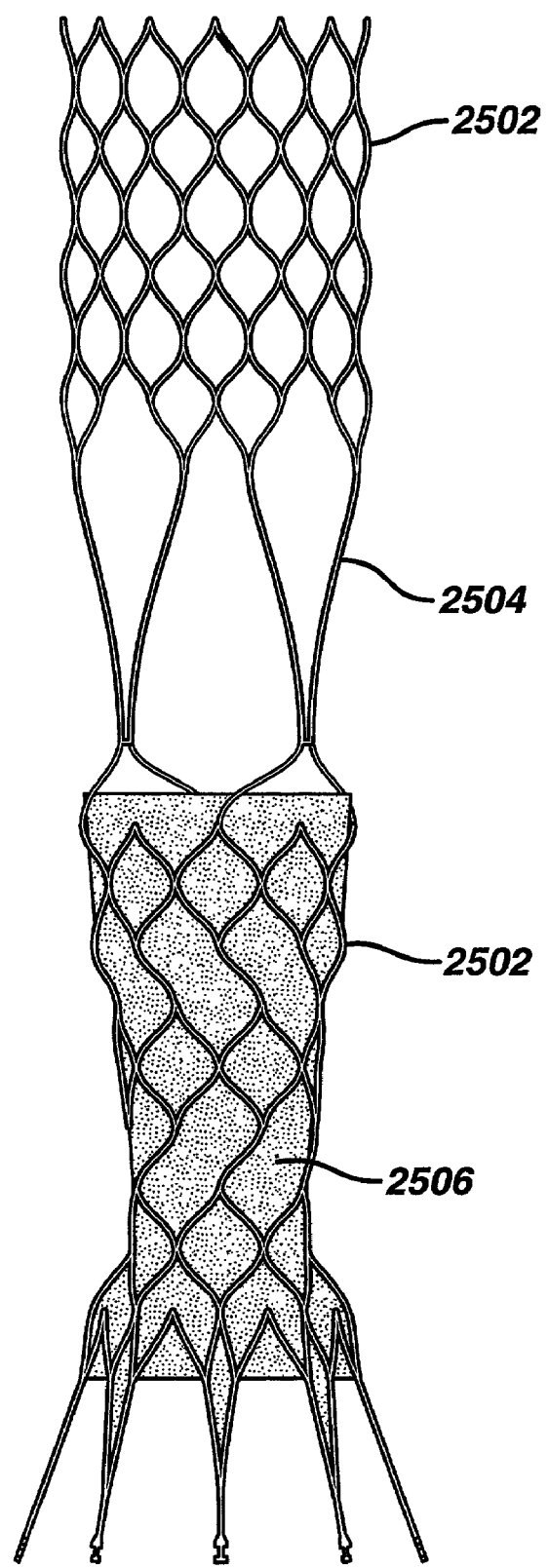
FIG. 28 is a side elevational view of the supra-renal anchoring device of FIG. 25 taken along section line 28-28.

FIGS. 20-24 illustrate yet another alternate exemplary embodiment of a supra-renal anchoring stent gasket 2000. The exemplary supra-renal anchoring stent gasket 2000 is similar in design to the exemplary embodiment illustrated in FIGS. 17-19 but is longer to increase its flexibility and anchoring and sealing functions. The struts 2002 are once again configured such that the upper struts 2006 are thicker than the lower struts 2008 as illustrated in detail in FIGS. 21 and 22. In this design, however, both the upper and lower sections of the stent gasket 2000 are constructed in a similar manner. However, as illustrated in FIG. 22, the stent gasket 2000 may comprise a taper. In addition, the gasket material 2010 is formed into two substantially tubular sections 2012 as illustrated in detail in FIG. 24. Additional gasket material 2014 may be utilized to fill in the space between the substantially tubular sections 2002. Alternately, the entire gasket material may be formed as a single, unitary structure. Once again the stent gasket 2000 may comprise recapture legs 2016 with flanges 2018.

FIGS. 25-28 illustrate yet another alternate exemplary embodiment of a supra-renal anchoring stent gasket 2500. In this exemplary embodiment some of the sections of the stent gasket 2500 have missing struts 2502. In addition, certain struts are thinner than other struts to increase flexibility. The thinner struts are the struts connected to legs 2504 described below. The missing struts and variable strut thickness designs are illustrated in detail in FIGS. 26 and 27. The missing struts are in the distal portion of the stent gasket 2500 to increase the flexibility of the distal portion. This exemplary embodiment is similar to the design illustrated in FIG. 15 in that the stent gasket comprises two distinct sections connected by a plurality of struts or legs 2504 and having a lower section having a gasket material 2506. Once again the stent gasket 2500 may comprise recapture legs 2508 with flanges 2510.

Second Prosthesis

The second prosthesis is a bypass conduit or the like that is typically deployed in an arterial passageway upstream of an aneurysm, and establishes a fluid flow path through the system or a portion thereof. In some embodiments of the invention, the second prosthesis defines a fluid flow path that passes through the arterial segment having the aneurysm, e.g., bypassing the aneurysm. In these embodiments of the invention, the second prosthesis extends from a healthy portion of the artery, through the arterial segment having the aneurysm, and into another healthy portion of the artery or another artery. In some embodiments of the invention, the second prosthesis defines a fluid flow path from one portion of the system, e.g., a proximal portion or end, to another portion, e.g., a distal portion or end, or an intermediate portion.

The second prosthesis functions to bypass the aneurysm, and to properly position and/or anchor the distal end of the system in an artery. The second prosthesis may also include one or more structures for positioning and anchoring the second prosthesis in the artery or in the first prosthesis. In one exemplary embodiment of the invention, the second prosthesis is adapted to engage the first prosthesis.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component. In preferred embodiments of the invention, fluoroscopically identifiable sutures or staples are used; these sutures or staples may also attach the graft material to the stent.

FIGS. 1, 4, 8, 9 show exemplary second or bypass prostheses 11(*a*,*b*?) of the present invention. Second prosthesis 11*a*, 11*b* includes a substantially cylindrical self-expanding lattice, support, or stent 40, typically made from a plurality of interconnected struts 44. Lattice 40 defines an interior space having two open ends, a proximal end 41 and a distal end 42. The interior and/or exterior surfaces of lattice 40 may be covered by or support at least one graft material 60.

The second prosthesis typically includes a support matrix or stent that supports a graft material. One end of the second prosthesis is typically adapted to engage one or more portions of a first prosthesis. In preferred embodiments of the invention, the proximal end of second prosthesis is adapted to matingly engage a proximal portion of the first prosthesis. The second prosthesis may optionally include at least one attachment structure on its distal end for engaging and securing the prosthesis in a portion of an artery downstream of the aneurysm. These and other features of the second prosthesis will be described in more detail below.

Stent

Any of the stents of the present invention form a support or lattice structure suitable for supporting a graft material. In preferred embodiments of the invention, the stent defines a channel through which a fluid, such as blood, may flow. A typical stent comprises an expandable lattice or network of interconnected struts. In preferred embodiments of the invention, the lattice is laser cut from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In some exemplary embodiments of the invention, the struts of the stent gasket form a matrix having diamond shapes. In the exemplary embodiment of the invention shown in FIG. 2, the matrix or struts of stent 10 is configured into a diamond shapes, preferably having approximately eight diamonds. In a most preferred embodiment of the invention, the fully expanded diamond pattern of a first prosthesis has angles of about forty-five to fifty-five degrees at their distal and proximal ends. In the exemplary embodiment of the invention shown in FIG. 4, the matrix or struts of stent 40 may be configured into at least two hoops 43, each hoop 43 comprising a number of struts 44 having a diamond shape, having approximately nine diamonds. A second prosthesis, such as second prosthesis 40, may further include a zigzag shaped ring 50 for connecting adjacent hoops to one another. The zigzag shaped rings may be formed from a number of alternating struts 52, wherein each ring has fifty-four struts.

The diamond pattern for the anchors, as well as the other hoops, provide the hoops with radial and longitudinal stiffness. The longitudinal strength provides for better mechanical fixation of stent 40 to a graft material (described below). The radial strength provides the proximal hoop 45 with better attachment and sealing to the gasket material, and provides the distal hoop 46 with better fixation and sealing to the arterial wall. Further, the distal hoop may be flared, and may be exposed after the graft material has been attached to the stent.

In one preferred embodiment, the proximal and distal hoops have greater radial and longitudinal strength than the hoops therebetween. This creates a stent graft having stiff ends for anchoring, but a more flexible body for navigation through the vasculature. The stiffer ends may be accomplished by changing the dimensions of the struts for the end hoops, or by varying the heat treatment of the end hoops during manufacture. The rings allow the stent to bend more easily, and generally provide for more flexibility when the stent is being delivered through a tortuous vessel. When a non-compliant graft is attached to a stent, the strength of the diamond hoops scaffolds any graft folding into the blood flow lumen, while maintaining a tight kink radius.

In accordance with some embodiments of the present invention, the proximal and/or distal end of a stent may include one or more anchors and/or one or more struts of the stent configured into an anchor. One or more anchors, commonly referred to as recapture legs, may also be configured to releasably engage a delivery device, such as a catheter, or a portion thereof. The distal end of the stent is preferably configured to engage a complementary structure on a delivery device, such as a catheter or a portion thereof.

Figure 7:
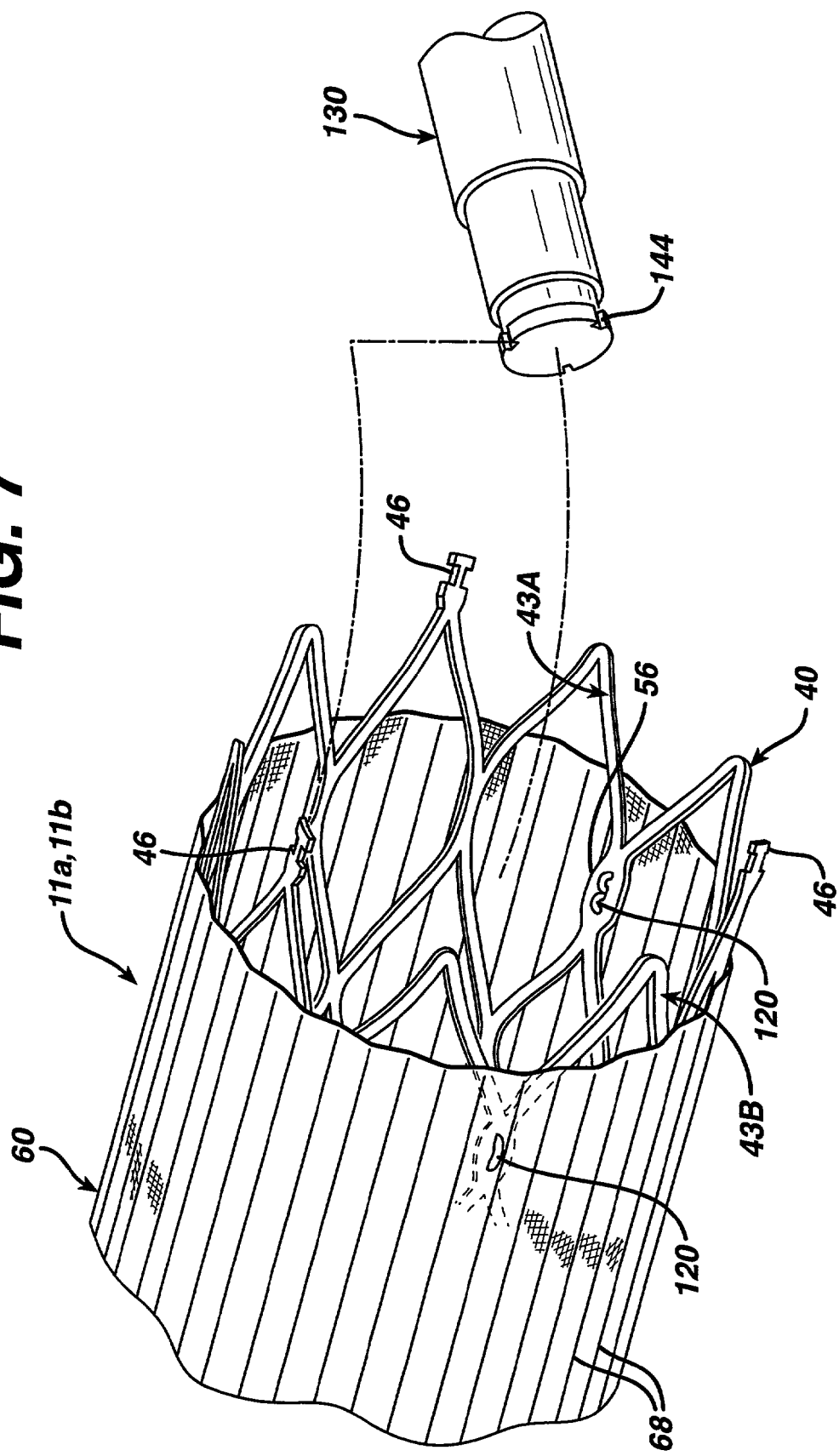
FIG. 7 is a partial, exploded perspective view of the distal end of a second prosthesis of the present invention illustrating an anchoring and delivery system according to the invention.

For example, the distal end of the stent may include one or more keys that engage, preferably releasably engage, a corresponding latch on the catheter. An exemplary configuration is shown in FIG. 7. It is intended that the invention should not be limited by the precise structures used to engage the stent to the delivery device.

In the exemplary embodiments of the invention shown in FIGS. 2,4,7,10 and 11, the stent may include one or more anchors 46 configured to engage a corresponding structure on a delivery device 130. In accordance with the present invention, the delivery apparatus may include a collar having one or more grooves or the like adapted to releasably engage one or more complementary structures on a stent or prosthesis of the present invention. For example, the delivery apparatus shown in FIG. 7 includes eight grooves 144 to configure the delivery device to releasably engage both the first prosthesis 10 in FIG. 1 (having eight anchors 46) and the second prosthesis 11a,b in FIG. 7 (having three anchors 46). Such an anchor/delivery device configuration is particularly suited to partially deploying a prosthesis of the present invention, and to position or re-position the prosthesis.

Any of the stents of the present invention may be formed from any material suitable for functioning in vivo as a support for graft material. A stent of the present invention may be formed from a wide variety of materials, all of which are well known to those skilled in the art. In some embodiments of the invention, the stent is formed from a metal or metal alloy. In preferred embodiments of the invention, the stent is formed from superelastic Nickel Titanium alloys (Nitinol). Descriptions of medical devices which use such alloys can be found in U.S. Pat. No. 4,665,906 and European Patent Application EP 0928606, both of which are hereby incorporated herein by reference. A stent according to the present invention is preferably laser cut from a tubular piece of nitinol and thereafter treated so as to exhibit shape memory properties at body temperature. In preferred embodiments of the invention, the stent material is expandable or collapsible, i.e., moveable from a first closed position to a second open position, or vice versa.

Graft Material

An inner or outer surface of a stent of the present invention may be covered by or support a graft material. Graft material 60 can be made from any number of materials known to those skilled in the art, including woven polyester, Dacron®, Teflon®, polyurethane, porous polyurethane, silicone, polyethylene terephthalate, expanded polytetrafluoroethylene (ePTFE) and blends of various materials.

In some embodiments of the invention, it may be desirable to incorporate a biodegradable, or degradable material, such as albumin, collagen or any type of collagen. A graft material that is biodegradable would erode or dissolve over time; however, it is believed that the eroding graft material may be replaced by one or more biofusion constituents, or alternately, a layer of endothelium may grow as the graft material erodes. It is further believed that these new layers of endothelium may provide a new, fluid impervious lining within the aneurysm.

It is preferred that all of the foregoing materials be porous to allow for an intimal layer to form a biofusion structure or matrix.

The graft material may be variously configured, preferably to achieve predetermined mechanical properties. For example, the graft material may incorporate a single or multiple weaving and/or pleating patterns, or may be pleated or unpleated. For example, the graft may be configured into a plain weave, a satin weave, include continuous longitudinal pleats, interrupted pleats, annular helical pleats, radially oriented pleats, or combinations thereof. Alternatively, the graft material may be knitted or braided. In the embodiments of the invention in which the graft material is pleated, the pleats may be continuous or discontinuous. Also, the pleats may be oriented longitudinally, circumferentially, or combinations thereof.

Figure 4:
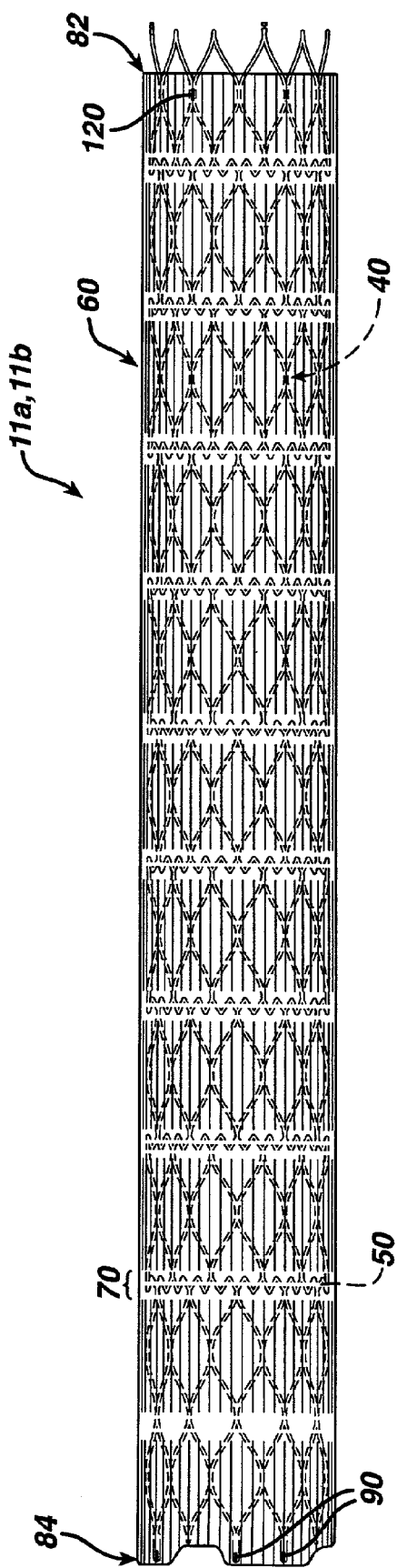
FIG. 4 is a side elevation of a second prosthesis having a stent covered by a graft material.
Figure 5:
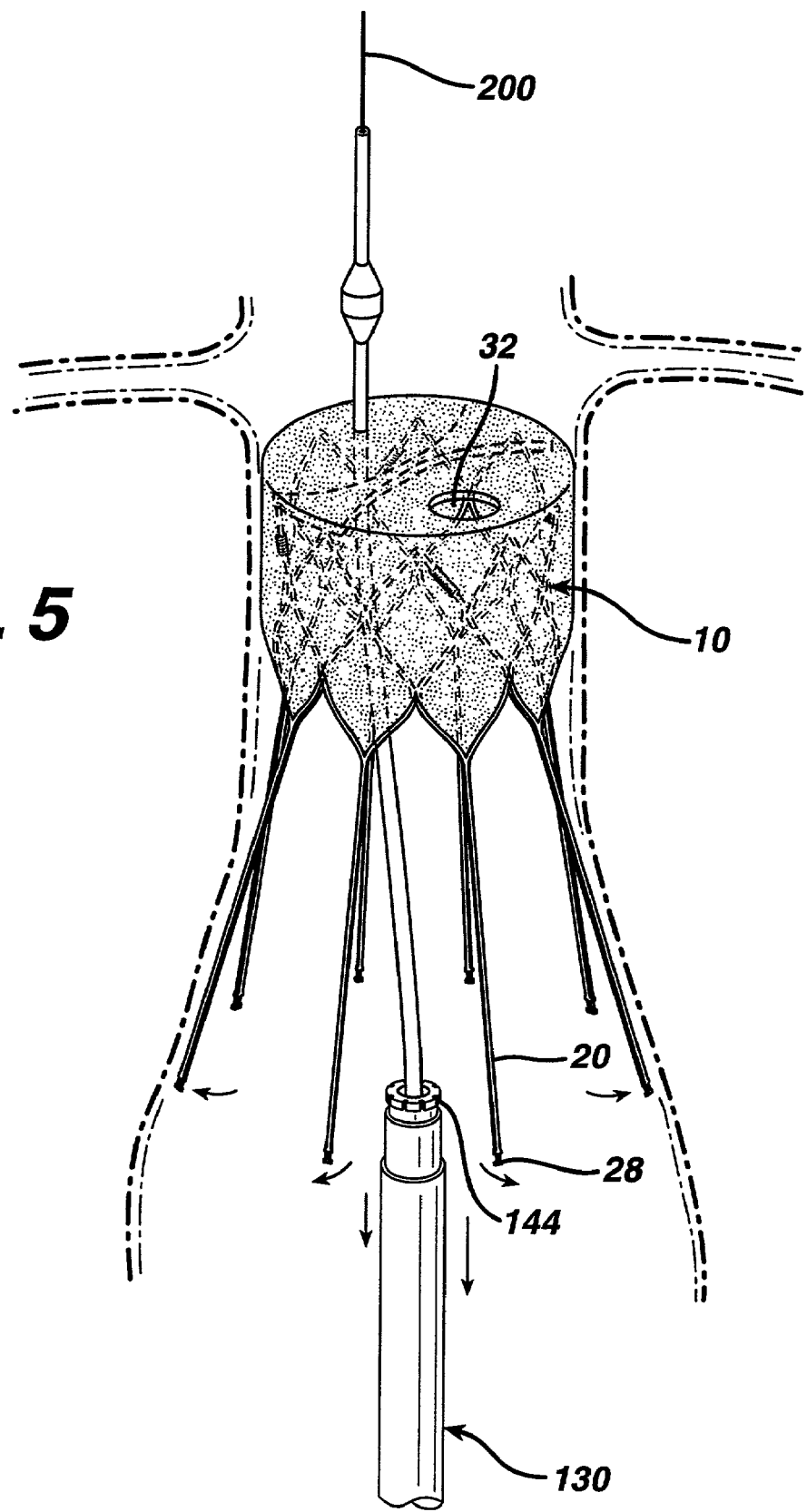
FIG. 5 is an elevation view of a fully deployed first infra-renal prosthesis made in accordance with the present invention and an exemplary delivery system.

As shown in FIG. 4, graft material 60 may include a plurality of longitudinal pleats 61 extending along its surface, generally parallel to the longitudinal axis of the prosthesis. As shown in FIG. 6, the pleats allow the prosthesis to collapse around its center, much as it would be when it is delivered into a patient. As illustrated, the pleats come together as a series of radially oriented regular folds that pack together efficiently. This provides a relatively low profile delivery system, and provides for a controlled and consistent deployment therefrom. It is believed that this configuration minimizes wrinkling and other geometric irregularities. Upon subsequent expansion, the prosthesis assumes its natural cylindrical shape, and the pleats or folds uniformly and symmetrically open.

In addition, pleats 61 help facilitate stent graft manufacture, in that they indicate the direction parallel to the longitudinal axis, allowing stent to graft attachment along these lines, and thereby inhibiting accidental twisting of the graft relative to the stent after attachment. The force required to push the stent-graft out of the delivery system may also be reduced, in that only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

As shown in FIGS. 4 and 9, the graft material may also include one or more, and preferably a plurality of, radially oriented pleat interruptions 70. The pleat interruptions are typically substantially circular and are oriented perpendicular to longitudinal axis. Pleat interruptions 70 allow the graft and prosthesis to bend better at selective points. This design provides for a graft material that has good crimpability and improved kink resistance.

As noted above, the extension prosthesis may be pleated longitudinally, axially, or combinations of both. Under typical conditions, these pleats will form a relatively consistent pattern, e.g., pleats all of a certain length. In the exemplary embodiments of the present invention for use in a highly angulated artery, it may be desirable to vary the pattern or patterns of pleats. For example, in the area of greatest angle, it may be desirable to provide an extension prosthesis having one or two (or more, as needed) pleat interruptions or axially pleated sections separated by a shorter longitudinally pleated section or sections. It is believed that increasing the number of axial pleats in the highly angulated section of the artery reduces stress on the prosthesis, and may promote a more fluid tight fit of the system.

The graft material as described above is preferably highly compressible, which also promotes a low crimped profile for better delivery characteristics.

In accordance with the present invention, the graft material may be impervious or substantially impervious to the flow of blood, or may be porous. A graft material is impervious if it prevents blood from passing through the graft material on contact with blood or after the graft material is saturated with blood. Choice of the flow characteristics of a graft material are well known to those skilled in the art, and are tied in part to the intended function of the prosthesis or portion of the prosthesis. For example, it may be desirable for the graft material that forms the cover of the first prosthesis to be impervious or substantially impervious to the flow of blood. Alternately, it may be desirable for a graft material to be porous or partially porous to promote biofusion.

In addition, it is preferable that the gasket member be substantially impervious to the flow of blood, at least when in a partially compressed state. When used throughout for the present invention, materials which are substantially impervious to the flow of blood include materials which become substantially impervious to the flow of blood after being saturated with blood.

The foregoing graft materials may be knitted or woven, and may be warp or weft knitted. If the material is warp knitted, it may be provided with a velour, or towel like surface, which is believed to speed the formation of blood clots, thereby promoting the integration of a prosthesis or prosthesis component into the surrounding cellular structure.

A graft material may be attached to a stent or to another graft material by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; and staples.

As stated above, a stent preferably has a graft member attached thereto. The graft member covers at least a portion of the interior or exterior of the stent, and most preferably covers substantially all of the exterior of the stent. In some embodiments of the invention, prosthesis 11a,b includes graft material 60 that covers only a portion of the distal end 42 of matrix 40. See, for example, FIG. 4.

In an alternate design, graft material may not be utilized on either end of the stent. For example, on any endolgegs, prosthesis, extension cuffs, stent gaskets or other covered stents, both ends thereof may be left uncovered. The biological body has the ability to cover the exposed portions of the stent with endothelial cells and thus these exposed portions become endothelialized or incorporated into the vessel wall. This may be an important factor in the long term stability of the system. Essentially, over long periods of time, the aneurysmal sac can and will shrink if it is totally excluded from blood flow. This shrinkage changes the morphology of the aortic region that has been treated with the bypass prosthesis. If all ends of the system are firmly anchored in the actual vessel, as is the case when the ends are covered with endothelium cells, the system will be better able to withstand these morphological changes.

In accordance with the present invention, it may be highly desirable to provide a graft material that limits or eliminates the amount of blood that passes between the graft and the arterial wall, to provide a catheter-delivered graft or prosthesis that extends through a longer portion of an artery, to improving the anchoring mechanisms between two prostheses, to improving the anchoring mechanism between the prosthesis and the arterial wall or an interluminal cavity within an artery, and to improve the fluid dynamic and performance characteristics if the implanted prosthesis.

Marker

As noted above, a stent and/or prosthesis of the present invention may include one or more markers. One skilled in the art will recognize that one or more markers may be positioned on the stent, the graft material, or on the prosthesis. In preferred embodiments of the invention, the markers are used to identify the position of the stent or prosthesis in relation to a body part and/or in relation to another stent or prosthesis, and/or to identify the position of one part of the prosthesis relative to another part. In most preferred embodiments of the invention, the marker(s) is used to identify a position in vivo.

As shown in FIGS. 2 and 3, a stent, such as stents 12 and/or 40 (FIG. 4), preferably includes one or more radiopaque markers 15. Exemplary materials for forming markers include but are not limited to tantalum, platinum, iridium, and gold. As shown, markers 15 are coils of radiopaque metal, wrapped around the struts of the stent. Markers 15 are preferably made from 0.0075 inch diameter tantalum (Ta) wire wrapped tightly around the struts.

The number, location, and size of the markers may vary, and the markers may be used alone or in combination to identify the position of a particular portion of the prosthesis. For example, a proximal marker adjacent aperture 32 may be five mm long and the proximal marker adjacent hole 33 may be two mm long. Also, two distal markers may be one hundred eighty degrees apart, and a proximal marker may be positioned equidistant from each of the distal markers. In this exemplary configuration, the proximal marker then aids proper rotational positioning of the device.

Connectors

Some exemplary embodiments of a prosthesis according to the present invention may include one or more connectors. In some embodiments of the invention, the connectors are used to engage or connect one prosthesis or component to another. In some embodiments of the invention, the connectors may be used to attach the gasket material or graft material to a stent or lattice.

As noted above, one skilled in the art will recognize that a variety of materials and methodologies may be used to connect one prosthesis to another, or to attach the graft material to a stent. Exemplary connectors include but are not limited to sutures, staples, rivets, or the like. In preferred embodiments of the invention, the connector is a suture or staple, even more preferably, having a knotted or nub end. Further, a connector may be formed from a radiopaque material or a fluorescent material, each of which allow the connector to be used as a marker.

In accordance with the present invention, it may be desirable to incorporate in a prosthesis a connector adapted for use with a lattice-like stent. A first connector 54, an exemplary embodiment of which is shown in FIG. 4, may be configured for use at an end portion of a stent, preferably at an end portion of a strut 44. A second connector 56, an exemplary embodiment of which is shown in FIGS. 4 and 7, may be configured for use at an internal portion of a stent, preferably at the junction between two struts 44.

A connector configured for receiving a rivet, staple, suture, or the like, may include two apertures, each aperture configured to receive a leg of the rivet, staple, suture, or the like. In this embodiment of the invention, the end of each leg is preferably formed into a knot, nub or spherical end that is of larger diameter than the diameter of the aperture. Preferably, all of the elements noted above are assembled, the legs are passed through the apertures, and the end of each leg is formed into a nub. Alternatively, one end may be formed into a nub prior to placement through the aperture, with the second end being formed into a nub after assembly of all the elements.

The number of connectors and staples are typically dictated by the size and structure of a particular stent; it is intended that the invention should not be limited thereby. The illustrated embodiments show six first connectors and three second connectors.

The above staple aperture design or connector assembly has many advantages for attaching gasket material or a graft material to a stent. Because the legs of the staple are folded around and imbedded within a pocket or the like, any risk of puncturing an inflation balloon is minimized. In addition, the structural integrity of the prosthesis is increased because staples more securely attach the graft material to the stent, as compared to prior art designs which use suture or adhesives to attach the graft to the stent.

Staples 90 and 120 may be made from any number of materials known in the art, including tantalum alloys, platinum alloys or stainless steel, such as a grade of type 316 stainless steel. The staples may take on other configurations and shapes, and can be coated for lubricity purposes, wear resistance and for the prevention of corrosion. Essentially, the coating may be used for increased durability. The staples may be formed from a radiopaque material to identify the location of the staple, and to act as a marker to identify the location of a portion of the prosthesis. Using a different number of radiopaque staples on a distal end of a stent as compared to a proximal end further assists in identifying the position of the prosthesis.

Methods

A method in accordance with the present invention includes delivering and positioning a system or component of a system in a fluid conduit, such as an aorta. The components described above permit intraluminal delivery into an aorta. This is accomplished by percutaneously inserting the prostheses into the same or different arteries, e.g., a femoral artery, and navigating them to the site of the aneurysm. This type of procedure is similar to delivery of angioplasty catheters and guiding catheters into the human vasculature. Upon proper positioning, the system components may be deployed either through a radially, outwardly extending force, e.g., expanding a balloon, or, if a self-expanding stent, by releasing the stent anchors from a constraint. Once fully deployed, at least one passageway is formed bypassing the aneurysm. As shown in FIG. 1, it may be desirable to form two fluid flow paths bypassing the aneurysm, each fluid flow path extending into a separate downstream artery.

In preferred embodiments of the invention, the first prosthesis is a stent gasket, even more preferably, a stent gasket that expands automatically against the wall of the artery. As the stent gasket expands, proximal longitudinal legs allow the stent gasket diamond rings to expand, thereby anchoring the stent in place. The method also includes delivering and positioning at least one second prosthesis. In preferred embodiments of the invention, the second prosthesis is a bypass conduit for extending through an aneurysm. The second prosthesis is typically positioned within the first prosthesis, preferably into and through a hole in the first prosthesis cover. In most preferred embodiments of the invention, the hole is slightly smaller in diameter than the expanded diameter of the second prosthesis, thus sealingly engaging the second prosthesis in the first prosthesis. The sealed configuration of the second prosthesis within the first prosthesis forms a fluid pathway through the assembly or system, thereby bypassing the aneurysm.

FIGS. 1, 8, and 9 generally show how the system of the present invention may be deployed in vivo. One skilled in the art will readily recognize that a typical delivery device, such as a catheter, includes a guidewire or the like that passes through an aperture in the cover of the first prosthesis, and a collar or the like that releasably engages at least one anchor on the prosthesis. Once the anchors are released from the collar, the first prosthesis can expand, preferably automatically. The portion of the delivery device containing the collar can then be removed from the artery, typically leaving the guidewire in place, i.e., still positioned in an aperture of the first prosthesis cover. The guidewire can then be used to guide another prosthesis or prostheses into position.

In some embodiments of the invention, the collar of the delivery device, engaged to the prosthesis, may be positioned within a sheath or the like until the prosthesis is delivered. In preferred embodiments of the invention, a portion of the prosthesis may be partially deployed and/or positioned. Once it is determined that the prosthesis is in its proper position, the collar can be pushed out of the sheath, thereby releasing the anchors from the collar. If the prosthesis is a self-expanding prosthesis, release of the flanges will allow the prosthesis to deploy automatically. If the prosthesis is not self-expanding, a deflated balloon or the like may be delivered to the interior of the prosthesis using the guidewire. When the balloon is inflated, it will expand the prosthesis into its fully deployed position, i.e., fully expanded radially.

As is evident to one skilled in the art, precisely placing a component(s) of the system may be critical. The physician must have precise placement of the components to ensure adequate repair of the aneurysm. The present invention allows the physician to fully deploy a component within the body without fully releasing the entire component from the delivery device. The anchors releasably interlock with complementary structures, such as grooves, on the delivery device, and, if the physician decides that the placement of the component is incorrect, the outer member of the delivery device may be moved relative to an inner member, thereby resulting in the prosthesis being retrieved or retracted within the delivery device. The extended legs and anchors allow the physician to temporarily position the prosthesis before full deployment. Once the physician is satisfied with a prosthesis' position, the legs 20 may be released from their engagement with the delivery device.

In order to prevent the physician from prematurely completely deploying a prosthesis, a releasable stop may be preferably placed on the delivery device.

In preferred embodiments of the invention, the system is used to bypass an abdominal aortic aneurysm (AAA). A method for treating or bypassing an AAA includes delivering, preferably percutaneously, a first prosthesis or precursor stent, or one of its components (e.g., the gasket member may be delivered separately, if desired). The components of the system are typically delivered through one of the femoral arteries and deployed within the infrarenal neck, between an abdominal aortic aneurysm and the renal arteries of a patient. Once the first prosthesis is properly positioned or re-positioned, the legs and anchors are fully released from the delivery device. The delivery device for the precursor stent may then be removed, without removing the guidewire, and another guidewire may be inserted through the other femoral artery and into first prosthesis. If the second guidewire is on the wrong side of the interior of first prosthesis, it will contact the occlusive member and be prevented from easily advancing. The physician may then properly reposition the guidewire through hole 32.

Thereafter each delivery apparatus, each containing a sheathed second prosthesis, is inserted into femoral arteries and by sliding them over the guide wires; each of the two second prostheses are then positioned in the first prosthesis. Thereafter, the second prostheses may be either separately or simultaneously deployed.

After proper delivery, precursor stent 10 and prostheses 11(*a*) and 11(*b*) should appear as they do in FIGS. 1, 8, and 9. First prosthesis 10 along with its attached gasket material 30 is firmly secured within an arterial section that includes the infrarenal neck 101, and may or may not include a portion of the abdominal aorta upstream of the renal arteries. In a preferred embodiment of the invention, a proximal portion of the first prosthesis is positioned upstream of the renal arteries, a distal portion of the first prosthesis is positioned downstream of the renal arteries, for example, in the infrarenal neck region, and an intermediate portion of the first prosthesis is positioned across the junction between the renal arteries and the abdominal aorta. The outward force of the second prostheses 11*a,b* on the precursor stent 10 helps to secure the device within the body. The distal ends of the second prosthesis may be firmly attached to the iliac arteries 1 and 2. Thereafter blood will flow from the abdominal aorta 302, through an exemplary system of the present invention comprising a first prosthesis and two second prostheses 11(*a*) and 11(*b*), and into iliac arteries 1 and 2, thereby bypassing the aneurysm 100.

In accordance with the present invention, a system and method for bypassing an aneurysm may establish one, and possible multiple, fluid flow paths through the system. When the system is placed in an artery upstream of a junction with one or more other arteries, the system permits fluid, such as blood, to flow through the proximal end of the system, and a portion of the blood may flow out of the system into one of the cross arteries. Another portion of the fluid will continue within the system, bypassing the aneurysm and out of the system into one or more downstream arteries. A method of the present invention therefore includes establishing one or more fluid flow paths. In a preferred embodiment of the invention, the method includes establishing a first fluid flow path through the system, wherein the first fluid flow path bypasses the aneurysm. The method may further include establishing at least one second fluid flow path, wherein the second fluid flow path passes through a portion of the system, and passes out of an intermediate portion of the system into an artery or arteries.

It is important to note that even though self-expanding stents are utilized, balloons may be utilized to over expand the stents for tacking them into position if necessary.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A system for bypassing an aneurysm comprising a first prosthesis and at least one separate and distinct bypass prosthesis, including at least one stent and graft material in fluid communication with the first prosthesis, the first prosthesis comprising a stent structure including a proximal section configured to engage a healthy section of artery above a branch artery upstream of an aneurysm, a distal section, and an intermediate section disposed between the proximal and distal sections, the proximal section comprising a substantially diamond like lattice configuration, the distal section comprising a substantially diamond like lattice configuration and a plurality of longitudinally extending legs, the intermediate section comprising a plurality of struts extending substantially orthogonal between the proximal and distal sections and configured to allow blood flow through the branch artery, the distal section comprising a sealing material attached thereto, the sealing material being distinct from the graft material and comprising a compressible foam, the distal section being configured to receive the at least one separate and distinct bypass prosthesis, the at least one separate and distinct bypass prosthesis passing through the distal section whereby the sealing material seals the first prosthesis to the wall of the artery and the first prosthesis to the at least one separate and distinct bypass prosthesis.

2. The system of claim 1 wherein a proximal portion of the distal section is configured to receive a proximal portion of the at least one separate and distinct bypass prosthesis.

3. The system of claim 1 wherein the distal section is configured to receive two separate and distinct bypass prostheses.

* * * * *